US006793488B1

(12) United States Patent
Houng et al.

(10) Patent No.: US 6,793,488 B1
(45) Date of Patent: Sep. 21, 2004

(54) FLAVIVIRUS DETECTION AND QUANTIFICATION ASSAY

(75) Inventors: Huo-Shu H. Houng, Burtonsville, MD (US); Niranjan Kanesa-Thasan, Rockville, MD (US)

(73) Assignee: U.S. Army Medical Research & Materiel Command, Ft. Detrick, MD (US)

( * ) Notice: Subject to any disclaimer, the term of this patent is extended or adjusted under 35 U.S.C. 154(b) by 0 days.

(21) Appl. No.: 09/551,161

(22) Filed: Apr. 14, 2000

Related U.S. Application Data
(60) Provisional application No. 60/153,685, filed on Sep. 14, 1999, and provisional application No. 60/129,713, filed on Apr. 16, 1999.

(51) Int. Cl.[7] .......................... C12Q 1/68; C12P 19/34; C07H 21/04
(52) U.S. Cl. ................... 433/6; 435/91.1; 435/91.2; 536/23.1; 536/24.3
(58) Field of Search .................. 435/6, 91.1, 91.2; 536/23.1, 24.3

(56) References Cited

U.S. PATENT DOCUMENTS 5,939,254 A    8/1999   Ennis et al.

OTHER PUBLICATIONS

Accession No. U47032.*
V.T.K. Chow et al., 1993 "Use of NS–3 Consensus Primers for the Polymerize Chain Reaction Amplification and Sequencing of Dengue Viruses and Other Flaviviruses" Arch. Virol. 133, 157–170.
L. Fulop, et al., 1993 "Rapid Identification of Flaviviruses Based on Conserved NS5–Gene Sequences" Journal of Virol. Methods 44, 79–188.

(List continued on next page.)

Primary Examiner—W. Gary Jones
Assistant Examiner—Jehanne Souaya
(74) Attorney, Agent, or Firm—Venable

(57) ABSTRACT

A fluorescent DNA probes specific to the conserved terminal 3'-noncoding region (nucleotides 10653–10678) of dengue virus and a pair of flanking primers are designed to formulate a dengue specific fluorogenic polymerase chain reaction (PCR). Optimal assay conditions with zero background are disclosed which permit the detection of low levels of dengue virus from clinical specimens. Dengue virus isolates from different geographic regions can be universally detected and identified by the fluorogenic RT-PCR assay. Moreover, the assay is specific for dengue 2 virus and does not recognize other related flaviviruses, including dengue serotypes Louis encephalitis, yellow fever, and Kunjin viruses. The ) 3, and 4, Japanese encephalitis, St. assay also efficiently detected immunocomplexed dengue viruses. The fluorogenic RT-PCR assay readily detected viremia in sera collected from individuals ill with dengue fever.

21 Claims, 8 Drawing Sheets

| DENGUE SEROTYPE DETECTION: | SEROTYPE-SPECIFIC UPPER PRIMERS: | INTERNAL FLUOROGENIC PROBE | LOWER PRIMERS (ANTI-SENSE, OR RT PRIMER) |
|---|---|---|---|
| DENGUE 1 | DV1.U  (SEQ ID NO:15)<br>5'-ACA-CCA-GGG-GAA-GCT-GTA-TCC-TGG-3' | | |
| DENGUE 2 | DV2.U  (SEQ ID NO:3)<br>5'-AAG-GTG-AGA-TGA-AGC-TGT-AGT-CTC-3' | DV.P1  (SEQ ID NO: 1)<br>5'-CTG-TCT-CCT-CAG-CAT-CAT-TCC-AGG-CA-3' | DV.L1  (SEQ ID NO:2)<br>5'-CAT-TCC-ATT-TTC-TGG-CGT-TCT-3' |
| DENGUE 3 | DV3.U  (SEQ ID NO:16)<br>5'AGC-ACT-GAG-GGA-AGC-TGT-ACC-TCC-3' | | |
| DENGUE 4 | DV4.U  (SEQ ID NO:17)<br>5'-AAG-CCA-GGA-GGA-AGC-TGT-ACT-CCT-3' | DV.P2  (SEQ ID NO:9)<br>5'-CTG-TCT-CTG-CAA-CAT-CAA-TCC-AGG-CA-3' | DV.L2  (SEQ ID NO:10)<br>5'-CAA-TCC-ATC-TTG-CGG-CGC-TCT-3' |

OTHER PUBLICATIONS

D.J. Gubler, 1989 "Surveillance for Dengue and Dengue Hemorrhagic Fever" Bull. Pan. Am. Health Organ. 23, 397–404.

E. Harris, et al., 1998 "Typing of Dengue Viruses in Clinical Specimens and Mosquitoes by Single-tube Multiplex Reverse Transcriptase PCR" J. Clin. Microbiol. 36(9), 2634–2639.

E.A. Henchal et al., 1990 "The Dengue Viruses" Clin. Microbiol. Rev. 3(4), 376–396.

C. W. Mudl, et al. 1998 "Spontaneous Engineered Deletions in the 3' Noncoding Region of Tick-borne Encephalitas VirusL Construction of Highly Atenuated Mutants of a Flavivirus" J. Virology, 72, pp. 2132–2140.

T.P. Monath, 1994 "Dengue: The Risk to Developed and Developing Countries" Proc. Natl. Acad. Sci. USA, 91, 2395–2400.

V. Proupski et al., 1999 "Biological Consequences of Deletions within the 3'–Untranslated Region of Flavivrus May Be Due to Rearrangements of RNA Secondary Structure" Virus Research, 64, pp. 107–123.

T.M. Sudiro et al., 1997 "Rapid Diagnosis of Dengue Viremia by Reverse Transcriptase–polymerase Chain Reaction Using 3'–noncoding Region Universal Primers" Am. J. Trop. Med. Hyg. 56(4), 424–429.

* cited by examiner

FIG. 8

FLAVIVIRUS DETECTION AND QUANTIFICATION ASSAY

CROSS-REFERENCE TO RELATED APPLICATIONS

This application is based on provisional application No. 60/153,685, filed on Sep. 14, 1999 and on provisional application No. 60/129,713, filed on Apr. 16, 1999, to which priority is claimed. The content of these documents is expressly incorporated herein.

TECHNICAL FIELD

The subject invention relates to a nucleic acid based diagnostic system for rapid and specific flavivirus virus identification and quantification and kits which involve a novel set of oligonucleotides which can distinguish and quantitate flavivirus, especially.

BACKGROUND ART

Dengue viruses belong to the family Flaviviridae, which contains almost 70 viruses, including those causing yellow fever and several encephalitides. Four distinct dengue virus types (dengue 2, 3, and 4) are each capable of causing infection in humans (Henchal and Putnak. 1990). Dengue infections are usually confirmed by serologic detection of dengue-specific antibodies or/and dengue virus isolation through culture in insect cells or mosquito inoculation (Gubler, 1989). These conventional methods for dengue virus detection are very time consuming, labor intensive, and have limited sensitivity for detecting low levels of dengue virus. Development of sensitive, type-specific dengue diagnostic systems is crucial because of explosive growth in dengue virus transmission and the increasing incidence of dengue hemorrhagic fever (Monath, 1994).

Rapid molecular diagnostic systems, such as RT-PCR, could provide a possible solution for dengue virus identification from clinical samples (Harris et al., 1998). Several RT-PCR systems for dengue virus detection have been reported, based on different conserved genomic regions, such as genes for nonstructural proteins (Chow et al., 1993; Fulop et al., 1993) and the 3'-noncoding region (Sudiro et al., 1997). See also U.S. Pat. No. 5,939,254. However, these methods frequently have mismatches corresponding to their amplicons, or even to primer sequences, due to genetic differences among strains of the same dengue serotype. Some of these systems rely upon sequences from the "conserved" regions for probes or primers, such as NS3 and NS5 genes. Alignment of these so-called conserved genes of dengue reveal mismatches among the viruses, in addition to variation among virus strains. These mismatches result in reduced sensitivity of the assay, and as a result, false diagnosis of the specific dengue virus. Further, unpredictable variations in PCR target sequences would yield lower specificity and sensitivity in dengue detection. In addition, these methods are often cumbersome to adapt for routine clinical use and are not quantitative.

The 3' noncoding region has been previously studied and sequenced. See, for example, Mandl, C. W., et al, "Spontaneous Engineered Deletions in the 3' noncoding region of Tick-borne Encephalitis Virus: Construction of Highly Atenuated Mutants of a Flavivirus", J. Virology, Vol. 72, (1998) pp. 2132–2140. Proupski, V. et al., "Biological Consequences of Deletions within the 3'-untranslated Region of Flavivirus May be due to Rearrangements of RNA Secondary Structure", Virus Research (1999) Vol. 64, pp. 107–123.

The invention herein disclosed addresses these and other associated problems.

DISCLOSURE OF THE INVENTION

The present invention is directed to designing and utilizing specific genomic region, the conserved 3'-terminal noncoding region, as specific nucleic acid-based diagnostic system for rapid and specific flavivirus, e.g. dengue virus, identification and quantification. In this regard, the invention focuses on the last 250, more specifically the last 200, even more specifically the last 160 bases of the conserved dengue genome corresponding to nucleotides 10558 through 10718 of dengue 1. The invention also utilizes flavivirus specific upstream primers, probes, and downstream primers developed from this region.

From the conserved terminal 3' non coding region conserved region, a probe unique to a flavivirus is chosen. Primers can then be generated from conserved areas upstream and downstream of the probe that are unique to the virus of interest, the areas extending to about one kilobase from the 3' terminus of any flavivirus. More than one primer set and more than one probe can be chosen, each primer set and probe can be both conserved and specific for a virus.

Once the cDNA is isolated from the samples containing the viruses to be identified, the cDNA is incubated with the primers and probe under condition such that a polymerase is able to synthesize a complementary strand using the primer/template substrate. The polymerase, having a 5'-to 3' exonuclease activity, will digest the probe hybridized to its specific complementary virus sequence. The probe may contain a reporter at the 5' end which will release a detectable signal when the probe is digested. Quantification and detection of the specific virus for which the probe and primers were designed is possible by detecting the released probe signal. If the probe does not find its match in the sample, the probe is not digested by the polymerase, and the signal is not released or detected.

The advantages of this invention are that probes can be highly discriminatory, even single nucleotide substitutions can be reliably detected among different viruses.

Oligonucleotide probes and primers described in this invention can be used in a multiplex format to detect and differentiate flaviviruses. It is also possible to formulate individual virus-specific assay mixtures to identify and quantitate one virus at a time. The format of the assay depends of the desired usage. A generic dengue diagnostic system may work well for clinical or epidemiologic use, whereas stereotype-specific dengue assays are required for use in vaccine development. The design of the assay can be refined for single-step multiplex use (processing of a specimen and evaluation in a single reaction mixture), or two step reactions may be used, as described in the material.

Applications of the Flavivirus Fluorogenic RT-PCR Assay

The flavivirus fluorogenic assays based on the terminal 3' noncoding region offer real-time quantitation of virions (expressed as plaque forming units or as genome copy equivalents). Determination of viral number is extrapolated from reproducible linear standard curves, derived either from titration of viral RNA or from dilutions of flaviviral cDNA (as plasmids). The rapid, sensitive detection of flaviviruses lends itself to several applications. These include:

1. Rapid diagnosis of flaviviral infection: the specific nature of the fluorogenic probes devised for this patent allows confirmation of flaviviral infection. Use of selected flaviviral probes (for example, for a particular geographic region) would support clinical/epidemiologic efforts to quickly and accurately establish the cause of specific illnesses such as febrile illness. Typically, the diagnostic apparatus required to confirm specific flaviviral infection is cumbersome and restricted to reference laboratories. The new methods allow rapid, bedside diagnosis and confirmation of flavivirus infection. This use will be greatly facilitated by the availability of portable field-tested diagnostic platforms during future deployments to endemic regions.

2. Determination of viral burden: the magnitude and duration of viremia during flaviviral infection may be positively associated with flaviviral pathogenecity. This finding may be of prognostic significance in dengue hemorrhagic fever, where increased viral burden (particularly at the time of defervescence) may be a marker of increased risk for severe disease. Studies of viral clearance by different immunologic mechanisms will be made easier. Furthermore, the effectiveness of specific antiviral therapy (such as drugs, immunotherapy, and other approaches) may be gauged by its effect on viral burden in vivo or in vitro.

3. Quality control of flaviviral biologics: the precise and specific determination of viral titer in flaviviral vaccines and other biologics is a difficult and time-consuming effort, often requiring three separate bioassays. The availability of a nucleic acid-based assay that is both specific and sensitive provides a significant advance in analysis (identification and characterization) of biologics, central to the quality assurance components of the manufacturing documentation required for any vaccine. Moreover, this methodology may be used with both live, recombinant, and killed flaviviral vaccines; it is also applicable to complex combinations of flaviruses, such as multivalent dengue vaccines.

4. Amplification of flaviviral RNA: the described method offers a simplified approach to creation of amplified, near full-length copies of flaviviral genomes. The 3' noncoding region is critical to replication of viral RNA, and the product of the reverse transcription reaction could be manipulated to generate flaviviral replicons. In addition, formation of replicative intermediates can be monitored through antisense RNA copies. Flaviviral cDNA products may be used for molecular pharmacologic or therapeutic purposes.

BRIEF DESCRIPTION OF THE DRAWINGS

Figure 8:
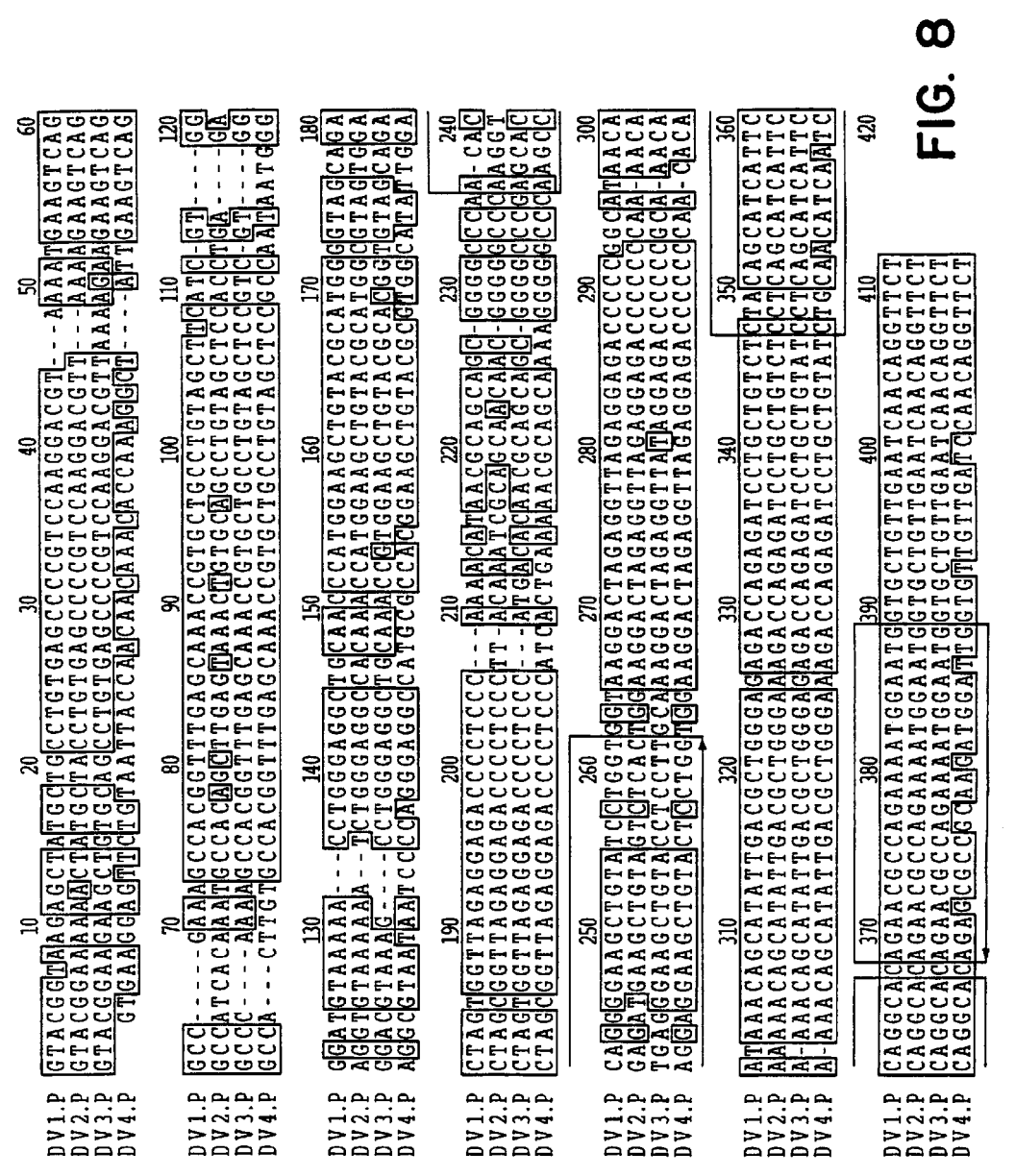

FIG. 8. Alignment of the #'-end sequences of dengue viruses, type 1, 2, 3, and 4 (SEQ ID NOS 18–21, respectively in order of appearance). Alignment of 3'-end sequences of dengue viruses, type 1, 2, 3 and 4. The gray area shows homologous sequences among different dengue serotypes. The last 160 bases of the conserved dengue genome corresponding to nucleotides 10558 through 10718 Of dengue type 1 are used to design serotyp specific Taqman probes and primers (shown in Table 2) to detect and differentiate dengue virus at the serotype level.

BEST MODE FOR CARRYING OUT THE INVENTION

Figure 1:
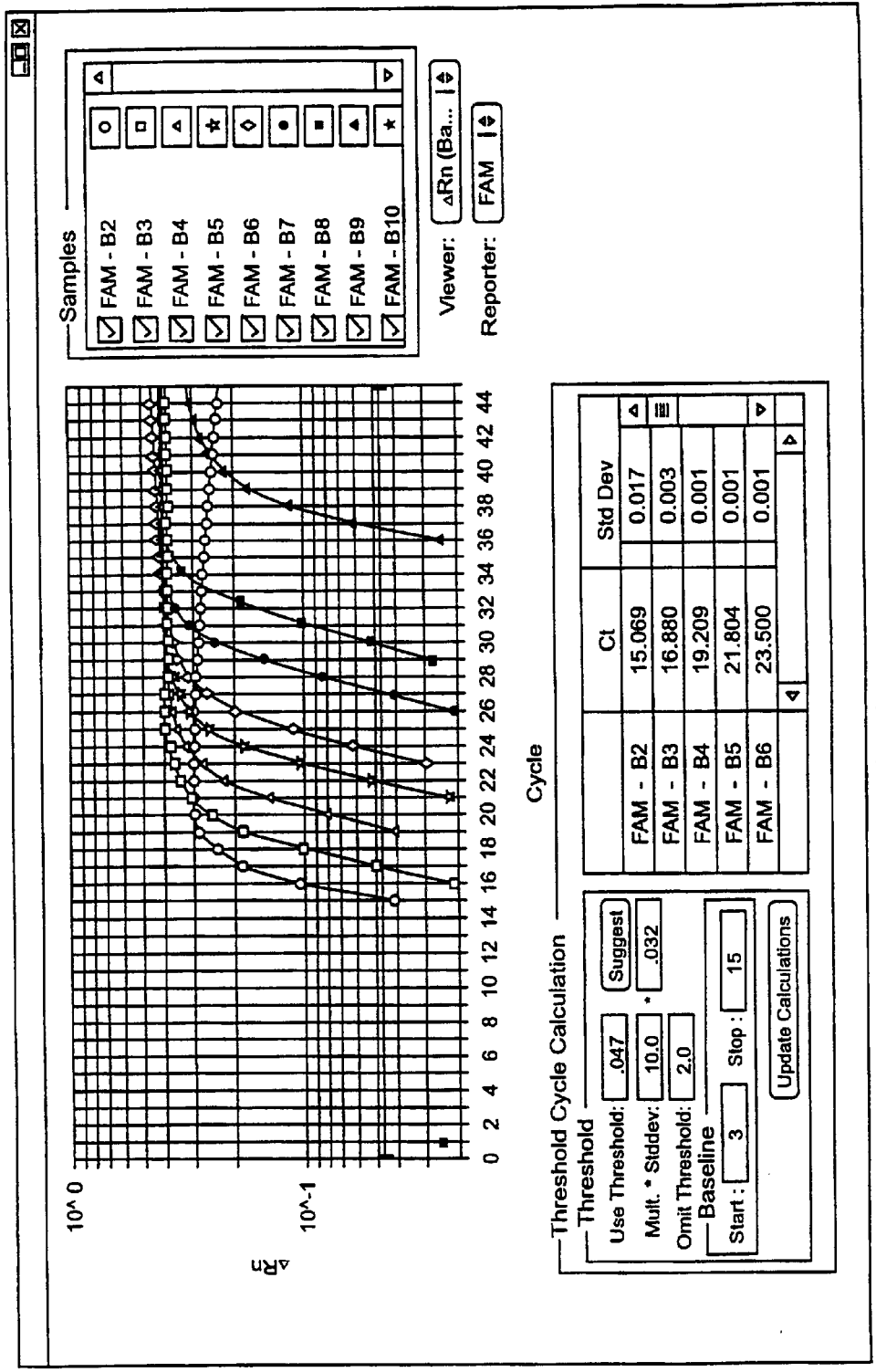
FIG. 1. Dengue 2 detection by fluorogenic RT-PCR. Seven 5-fold serially diluted cDNA derived from RNA extract of dengue 2 S16803 ($3.8 \times 10^7$ pfu/ml) were used as DNA template. Accumulation in fluorescence ($\Delta$Rn) as amplification progresses for each diluted cDNA are shown by different sigmoid plots. Two non-template controls are represented by two plots locating on the far right.

Dengue viral RNA was extracted from about 40 µl of either viral suspension or infected serum and then the total viral RNA was dissolved into buffer, and about 8 µl of the resulting RNA solution was mixed with about 12 µl of RT reaction mixture (see below). After reverse transcription, about 2 µl of the cDNA product was used as DNA template for the fluorogenic PCR assay. The total sample input for each fluorogenic PCR reaction was calculated as follows: 40 Iii specimen used for RNA extraction ×8 µl RNA used for RT/32 µl total RNA X 2 µl cDNA/20 µl total cDNA=1 µl of dengue 2 virus specimen.

For practical purpose, the expressed viral concentration is stated in terms of pfu per ml sample. The actual virus detected per PCR reaction should be only 1/1000 of dengue sample concentration, pfu/n-J. Based on the sensitivity defined in this study, the lower limit of dengue detection is only 0.01 pfu per PCR assay. It is not possible for any known PCR assay to detect fraction of integral genomic sequence. Thus, each infectious pfu for dengue virus should represent at least 100, or greater of genomic equivalencies.

According to the above general method, a novel dengue 2 type-specific genomic sequence derived from the 3' noncoding region (NCR) was use to develop a fluorogenic-based RT-PCR (Taqman, PE Biosystem, Foster City, Calif.). The assay was formulated to use a uniquely designed internal fluorescence labeled probe to specifically hybridize a 3'-noncoding target sequence of dengue 2. After hybridizing to the target PCR product, fluorescent signal is released through 5'-nuclease activity of DNA Taq polymerase that is used to amplify the target sequence (Holland et al. 1991; Higgins, et al. 1998). This allows convenient monitoring of a specific PCR product formation over time. In contrast to traditional dengue RT-PCR, the fluorogenic RT-PCR developed in this study is capable of discriminating single nucleotide substitutions in the target sequence. In this study, real time detection of dengue PCR product was correlated with input dengue cDNA copy number, to yield a quantitative assay for dengue 2 viruses.

Material and Methods

Viruses

Dengue virus strains and other flavivirus isolates shown in Table I were obtained from Departments of Virus Diseases and Biologics Research, Walter Reed Army Institute of Research, Washington, DC. Most virus isolates were routinely obtained from supernates of insect or Vero cell culture. Virus titrations were performed by plaque assay in Vero cells (Eckels et al., 1980). A dengue 2 S16803 virus stock suspension ($3.8 \pm 0.8 \times 10^8$, plaque forming units, pfu per ml) was used as a standard for development of the assay.

TABLE I

List of Flavivirus strains

| Virus | Strains | Origins | Comments |
|---|---|---|---|
| Dengue 1 | WP74 | West Pacific | WRAIR vaccine strain |
| Dengue 1 | Hawaii | Hawaii | |
| Dengue 1 | Haiti 059 | Haiti | |
| Dengue 2 | S16803 | Thailand | WRAIR vaccine strain |
| Dengue 2 | NGC | New Guinea | |
| Dengue 2 | SOM 13 | Somalia | Kanesa-thasan et al., 1998 |
| Dengue 2 | SOM 58 | Somalia | |
| Dengue 2 | Haiti 103 | Haiti | |
| Dengue 2 | Haiti 120 | Haiti | |
| Dengue 2 | Haiti 121 | Haiti | |
| Dengue 2 | 16681 | Thailand | |
| Dengue 2 | PRS-1 | Puerto Rico | |
| Dengue 2 | 21868 | Thailand | |
| Dengue 2 | ALI 088 | Brazil | |
| Dengue 2 | ALI 072 | Brazil | |
| Dengue 2 | ALI 013 | Brazil | |
| Dengue 3 | CH53489 | Thailand | WRAIR vaccine strain |
| Dengue 3 | H87 | Philippines | |
| Dengue 3 | SOM 79 | Somalia | |
| Dengue 4 | 341750 | Caribbean | WRAIR vaccine strain |
| Dengue 4 | H241 | Philippines | |
| Dengue 4 | Haiti 119 | Haiti | |
| Japanese encephalitis | $SA_{14}$-14-2 | China | |
| Yellow fever | 17D | Nigeria | |
| Kunjin | — | — | |
| St. Louis encephalitis | — | | |

Sera

Dengue infected human sera were collected from individuals with confirmed dengue fever in Somalia (Kanesa-thasan et al., 1994) and Haiti (Trofa et al., 1997). These specimens were dengue 2 positive by indirect immunofluorescence after culture in C6/36 insect cells. Monkey sera were obtained from three monkeys following subcutaneous inoculation with $10^4$ pfu dengue 2 virus S16803. Blood specimens were collected daily for 12 days after infectious challenge from each monkey. For immunocomplexed dengue virus study, pooled human hyperimmune serum with plaque reduction neutralizing antibody titer of 1:7000 against dengue 2 was kindly provided by the Dept of Virology, AFRIMS, Bangkok, Thailand. AU serum specimens were stored at $-80°$ C. until use.

Extraction of Viral RNA

Virus RNA used in this study was routinely extracted from virus suspensions or dengue-infected sera (40 VI) according to QiAamp Viral RNA Handbook (Qiagen Inc. Valencia, Calif. 91355). Total RNA was eluted into 32 µl of TE-(10 mM Tris-HCl, 1 mM $Na_2EDTA$, pH 8.0).

Design and Synthesis of Primers and Fluorogenic Hybridization Probe

An unique design of dengue 2 fluorogenic probe (DV2. PI) and its flanking primers (DV2. U2 and DV2.L1) based on its 3'-end genomic sequence (Genbank Accession # N120558) were selected by using Primer Express software (PE Applied Biosystems Inc., Foster City. These oligonucleotide sequences are shown as following: (SEQ ID NO:1) DV2.P1 (nucleotides 10653–10678): 5'-CTG-TCT-CCT-CAG-CAT-CAT-TCC-AGG-CA-3 (SEQ ID NO:2) DV2.L1 (nucleotides 10558–10579):5'-CAT-TCC-ATT-TTC-TGG-CGT-TCT-3 (SEQ ID NO:3) DV2.U2 (nucleotides 10680–10700): 5 '-AAG-GTG-AGA-TGA-AGC-TGT-AGT-CTC-'. DV2.P1 consists of oligonucleotide sequence shown as above with a 5'-reporter dye (FAM, 6-carboxy-fluorescein) and a down stream 3'-quencher dye (TAMRA, 6-carboxy-tetramethyl-rhodamine). Both labeled and non-labeled oligonucleotides were synthesized by Oligo-factory of PE Applied Biosystem Inc., Foster City, Calif.

Oligonucleotide Probes

The term "oligonucleotide" as used herein includes linear oligomers of natural or modified monomers or linkages, including deoxyribonucleotides, ribonucleotides, and the like, capable of specifically binding to a target polynucleotide by way of a regular pattern of monomer-to-monomer interactions, such as Watson-Crick type of base pairing, or the like. Usually monomers are linked by phosphodiester bonds or analogs thereof to form oligonucleotides ranging in size from a few monomeric units, e.g. 3–4, to several tens of monomeric units. Whenever an oligonucleotide is represented by a sequence of letters, such as "ATGCCTG," it will be understood that the nucleotides are in 5'.fwdarw.3' order from left to right and that "A" denotes deoxyadenosine, "C" denotes deoxycytidine, "G" denotes deoxyguanosine, and "T" denotes thymidine, unless otherwise noted. Analogs of phosphodiester linkages include phosphorothioate, phosphoranilidate, phosphoramidate, and the like.

As used herein, "nucleotide" includes the natural nucleotides, including 2'-deoxy and 2'-hydroxyl forms, e.g. as described in Komberg and Baker, DNA Replication, 2nd Ed. (Freeman, San Francisco, 1992). "Analogs" in reference to nucleotides includes synthetic nucleotides having modified base moieties and/or modified sugar moieties, e.g. described by Scheit, Nucleotide Analogs (John Wiley, New York, 1980); Uhlman and Peyman, Chemical Reviews, 90: 543–584 (1990), or the like, with the only proviso that they are capable of specific hybridization. Such analogs include synthetic nucleotides designed to enhance binding properties, reduce degeneracy, increase specificity, reduce activity as enzyme substrates, and the like.

Oligonucleotides of the invention can be synthesized by a number of approaches, e.g. Ozaki et al, Nucleic Acids Research, 20: 5205–5214 (1992); Agrawal et al, Nucleic Acids Research, 18: 5419–5423 (1990); or the like. The oligonucleotide probes of the invention are conveniently synthesized on an automated DNA synthesizer, e.g. a Perkin-Elmer (Foster City, Calif.) Model 392 or 394 DNA/RNA Synthesizer, using standard chemistries, such as phosphoramidite chemistry, e.g. disclosed in the following references: Beaucage and Iyer, Tetrahedron, 48: 2223–2311 (1992); Molko et al, U.S. Pat. No. 4,980,460; Koster et al, U.S. Pat. No. 4,725,677; Caruthers et al, U.S. Pat. Nos. 4,415,732; 4,458,066; and 4,973,679; and the like. Preferably, the oligonucleotide probe is in the range of 15–150 nucleotides in length selected from contiguous sequences in the conserved 3'- terminal non-coding region to detect and quantitate specific flaviviruses. More preferably, the oligonucleotide probe is in the range of 18–30 nucleotides in length. The precise sequence and length of an oligonucleotide probe of the invention depends in part on the nature of the target nucleic acid sequence to which it hybridizes. The binding location and length may be varied to achieve appropriate annealing and melting properties for a particular embodiment. Guidance for making such design choices can be found in many of the above-cited references describing the "Taqman" type of assays. The invention develops these probes from the last 250 nucleotides, more specifically the last 200 nucleotides; even more specifically the last 160 nucleotides of the 3' noncoding region of the flaviviral genome.

The oligonucleotide probes of the present invention include fluorescer and quencher molecules attached to the oligonucleotide. As used herein, the terms "quenching" or "fluorescence energy transfer" refer to the process whereby when a fluorescer molecule and a quencher molecule are in close proximity, whenever the fluorescer molecule is excited, a substantial portion of the energy of the excited state nonradiatively transfers to the quencher where it either dissipates nonradiatively or is emitted at a different emission wavelength than that of the fluorescer. It is well known that the efficiency of quenching is a strong function of the proximity of the fluorescer and the quencher, i.e., as the two molecules get closer, the quenching efficiency increases. As quenching is strongly dependent on the physical proximity of the reporter molecule and quencher molecule, it has been assumed that the quencher and reporter molecules must be attached to the probe within a few nucleotides of one another, usually with a separation of about 6–16 nucleotides, e.g. Lee et al. Nucleic Acids Research, 21: 3761–3766 (1993); Mergny et al., Nucleic Acids Research, 22: 920–928 (1994); Cardullo et al., Proc. Natl. Acad. Sci., 85: 8790–8794 (1988); Clegg et al, Proc. Natl. Acad. Sci., 90: 2994–2998 (1993); Ozaki et al, Nucleic Acids Research, 20: 5205–5214 (1992); and the like. Typically, this separation is achieved by attaching one member of a reporter-quencher pair to the 5' end of the probe and the other member to a base 6–16 nucleotides away.

The selection of appropriate fluorescer-quencher pairs for particular probes is well known in the literature. See, for example Wu et al., Anal. Biochem., 218: 1–13 (1994). Pesce et al., editors, Fluorescence Spectroscopy (Marcel Dekker, New York, 1971); White et al, Fluorescence Analysis: A Practical Approach (Marcel Dekker, New York, 1970); and the like. Fluorescer-quencher pairs may be xanthene dyes, including fluoresceins, and rhodamine dyes. Another group of fluorescent compounds are the naphthylamines, having an amino group in the alpha or beta position. Included among such naphthylamino compounds are 1-dimethylaminonaphthyl-5-sulfonate, 1-anilino-8-naphthalene sulfonate and 2-p-touidinyl-6-naphthalene sulfonate. Other dyes include 3-phenyl-7-isocyanatocoumarin, acridines, such as 9-isothiocyanatoacridine acridine orange; N-(p-(2-benzoxazolyl)phenyl)maleimide; benzoxadiazoles, stilbenes, pyrenes, and the like.

Reverse Transcription (RT) and Polymerase Chain Reaction (PCR)

Each viral RNA extract was transcribed into cDNA using Taqman RT kit (PE ABI, Foster City, Calif.). The RT reactions were performed in 20 W volume containing 8 $\mu$l extracted RNA, 2 41 1 0 ×RT buffer (PE ABI), 4 $\mu$l 2.5 mM dNTPs', 4.4 $\mu$l 25 MM $MgCl_2$, 0.4 $\mu$l RNAase inhibitor, 0.5 $\mu$l MuLV reverse transcriptase (50 units/ul), and 1 ul DV2.L1 primer (20 pmole/ul). RT reaction mixtures were incubated at 25° C. for 10 minutes followed at 48° C. for 30 minutes, then 95° C. for 5 minutes. The resulting cDNA was used as template in the subsequent PCR reaction.

PCR reactions were conducted in 50 VI volume containing 2.0 VI cDNA template, Taqman buffer (PE ABI, Foster City, Calif.), 0.1 mM deoxyribonucleotide triphosphates× (dNTPs), 2.0 MM $MgCl_2$, 200 nM DV2.U2, 20 nM DV2.P1, 60 nM DV2.L1, and 25 units AmpliTaq Gold DNA polymerase (PE ABI, Foster City, Calif.). Gene detection system 7700 and sequence detection system software version, 6.3 (PE ABI, Foster City, Calif.) were employed for PCR cycling reaction, real time data collection and analysis. 6 PCR mixtures were pre-incubated at 50° C. for 2 minutes, then 95° C. for 10 minutes followed by 40 cycles of two-step incubations at 95° C. for 15 seconds and 60° C. for 1 minute.

Results

Preliminary Observations

Real time amplification assays based on 3'-noncoding sequence of dengue 2 virus were initially demonstrated using serially diluted cDNA derived from RNA extract of 10 diluted dengue 2 S16803 stock ($3.8\times10^7$ pfulml). Seven 5-fold serial dilutions of viral cDNA were used as DNA templates for the dengue 2 fluorogenic RT-PCR assay. Figure shows typical sigmoid plots representing formation of the dengue 2 specific PCR product by accumulation in fluorescence ($\Delta$R) as amplification progresses (cycle number). Threshold Cycle ($C_T$) for each cDNA concentration is defined as cycle number where the sequence detection application software detects the increase of fluorescence associated with exponential growth of PCR product. The cycle number to yield detectable fluorescence level, $C_T$ usually was automatically selected by using the average of samples' fluorescences from cycle 3 through IS as the baseline shown in FIG. Parallel curves were derived from different concentrations of dengue 2 viral cDNA templates. Greater initial viral cDNA copy numbers required fewer amplification cycles (smaller $C_T$ value) to reach a detectable fluorescence level. As the number of viral copies was reduced by serial I dilutions, the curves corresponding to each individual dilution were shifted to the night, with greater $C_T$ values. The furthermost right plot, showing $C_T$ value of approximately 37, represents non-template (water) controls. These preliminary results established that the dengue 2-specific primers and the probe uniquely designed for the fluorogenic RT-PCR system are capable of detecting dengue 2 viral cDNA in a dose-dependent fashion over 7 serial 5-fold dilutions (more than 3.5 logs dilution). In addition, the assay is capable of discriminating specific dengue 2 viral stock cDNA from background levels (non-template controls).

Optimization of Dengue 2 Fluorogenic RT-PCR Assay

Figure 2:
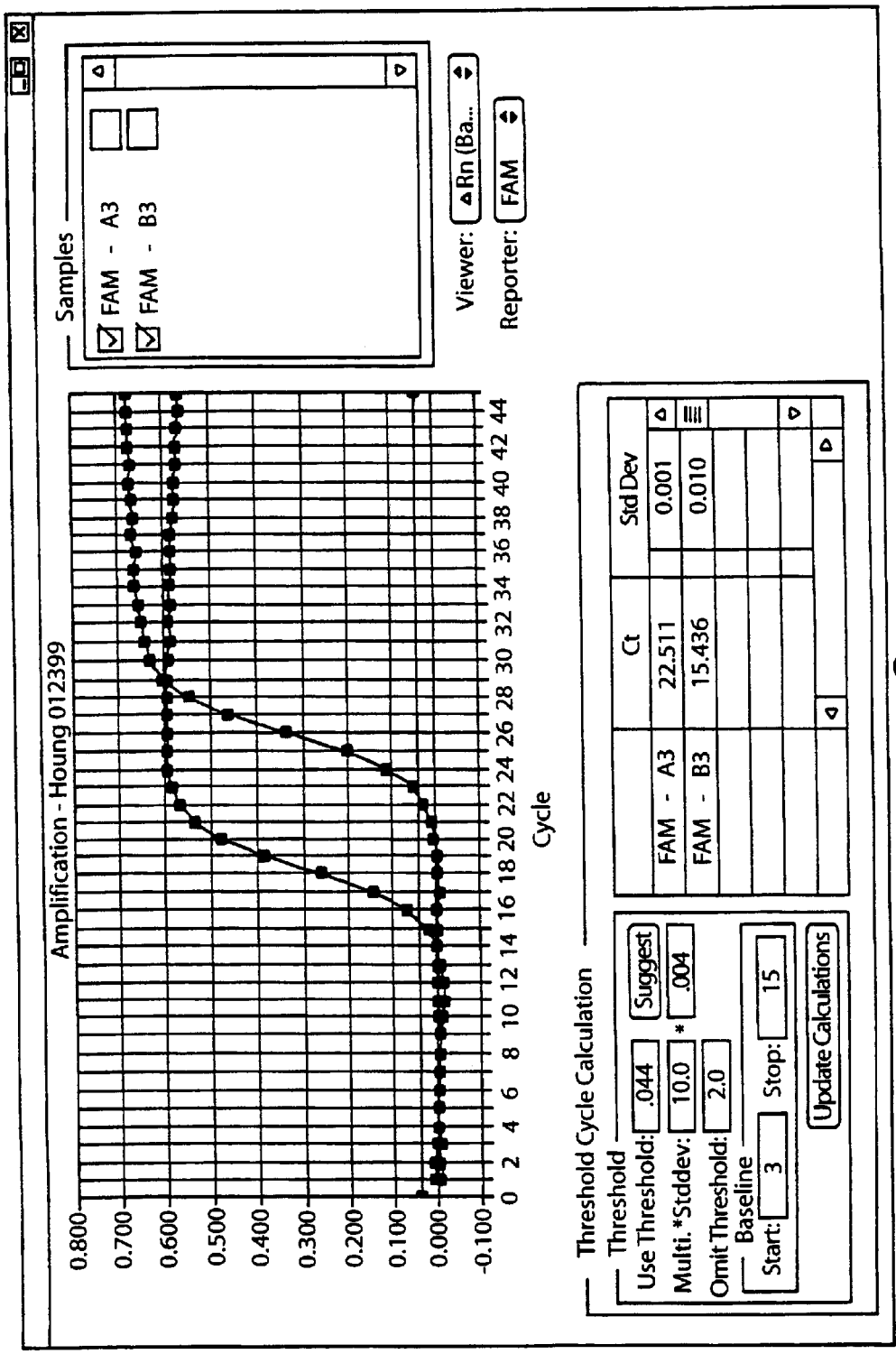
FIG. 2. Comparison of DV2.L1 and poly-oligo$(T)_{16}$ primers for reverse transcription reactions to generate cDNA from dengue 2 RNA. Fluorogenic PCR was conducted using cDNA of DV2.L1 and poly-oligo$(T)_{16}$.

The sensitivity of the assay can be improved by enhancing the relationship between dengue viral cDNA copy number and $C_T$ value. DV2.L1 primer was with universal poly-oligo (T)16 primer (PE Applied Biosystem Inc., Foster City, Calif.) for reverse transcription of dengue RNA. Universal poly-oligo (T)16 primer is frequently used as generic RT primer to generate dengue cDNA during reverse transcription process. The quantities of cDNA generated by RT reactions of the same dengue viral RNA (from dengue 2 virus suspension of $3.8 \times 10^6$ pfu/ml) were examined using DV2.L1 and poly-oligo (T),6 primers, respectively. FIG. 2 shows that use of DV2.L1 primer in the RT reaction yielded much greater number of cDNA copies than the poly-oligo (T)16 primer by dengue 2 fluorogenic PCR, i.e. $C_T$ of 15.4 vs. 22.5. Thus, DV2.L1 was used for all RT reactions in this study. The effects of varying the concentrations of $Mg^{++}$ on the PCR reaction were examined. It was shown in FIG. 3 that Mg' concentration from 1.5 to 2.5 mM had very little effect on the $C_T$ value of the assay. A midrange Mg concentration of 2.0 mM was selected as optimal for the assay.

The background (non-template control) was reduced by examining the effect of different concentrations and ratios of the flanking primers, DV2.L1 and DV2.U2, respectively. Preliminary observations showed that the dengue 2 fluorogenic RT-PCR would yield saturating, high fluorescence levels when DV2.U2 and DV2.L1 primers were used at equimolar concentrations of 200 nM (as shown in FIG. 1). However, under such conditions, non-template/water controls would yield detectable background fluorescent signal after 36 to 37 cycles of amplification. Little or zero background fluorescence level after 40 amplification cycles (defined as $C_T$ of 40 for non-template control wells) is desirable for dengue 2 detection from samples containing low virus concentrations. The optimized primer ratio was empirically determined as 200 nM for DV2.U2 primer and 60 nM for DV2.L1 primer. Using dengue 2-specific RT primer with optimal Mg" concentration and primer ratios, we demonstrated zero background RT-PCR assays (shown in sensitivity study, Table 2).

TABLE 2

$C_\tau$ values of spiked sera containing serially diluted dengue 2 S16803 stock.

| Samples/dilution | Calculated pfu/ml | Triplicate $C_\tau$ values | | | Average $C_\tau$ |
|---|---|---|---|---|---|
| 1:5 | $1.0 \times 10^6$ | 19.46 | 19.44 | 20.11 | 19.67 |
| 1:25 | $2.0 \times 10^5$ | 22.53 | 21.74 | 22.92 | 22.40 |
| 1:125 | $4.0 \times 10^4$ | 23.96 | 23.66 | 24.09 | 23.90 |
| 1:625 | $8.0 \times 10^3$ | 27.49 | 26.85 | 27.61 | 27.36 |

TABLE 2-continued $C_\tau$ values of spiked sera containing serially diluted dengue 2 S16803 stock.

| Samples/dilution | Calculated pfu/ml | Triplicate $C_\tau$ values | | | Average $C_\tau$ |
|---|---|---|---|---|---|
| 1:3125 | $1.6 \times 10^2$ | 28.90 | 27.91 | 28.11 | 28.31 |
| 1:15625 | $3.2 \times 10$ | 33.22 | 32.53 | 31.52 | 32.42 |
| 1:78125 | 6.4 | 37.14 | 36.74 | 35.79 | 36.55 |
| 1:390625 | 1.3 | 38.68 | 40.0 | 38.35 | 38.50 |
| 1:1953125 | 0.3 | 38.22 | 40.0 | 40.0 | 38.22 |
| NTC control | 0 | 40.0 | 40.0 | 40.0 | 40.0 |

Sensitivity and Specificity of Dengue 2 Fluorogenic RT-PCR

Figure 4:
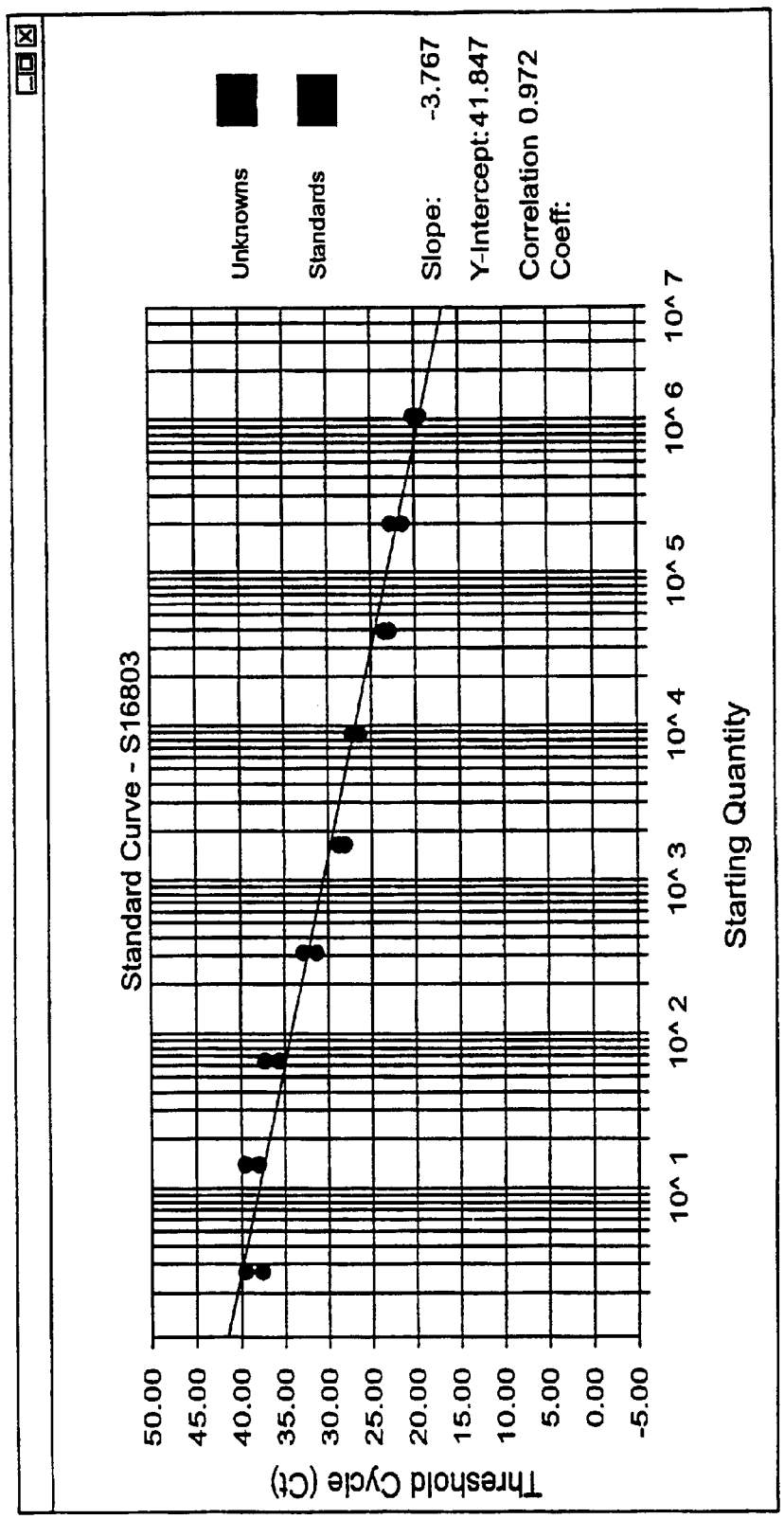
FIG. 4. Standard curve of dengue 2 S16803. Triplicate $C_T$ values of serially diluted S16803 ranging from 1.3 to $10^6$ pfu/ml are shown.

The upper and lower detection limits of the fluorogenic PCR assay were determined using optimized assay conditions identified in the previous section. Normal human sera were spiked with serial 1.5 dilutions of 1:100 diluted stock dengue 2 S 16803 virus suspension ($3.8 \times 10^6$ pfu/ml). The resulting ten spiked sera contained dengue 2 virus concentrations ranging from $0.3-10^6$ pfu/ml. Viral RNA extracted from each serum was used to generate cDNA as described in Materials and methods. Table 2 shows results of triplicate assays using cDNA derived from serially diluted dengue 2 virus standard, Consistent triplicate CT values were obtained for nearly the entire range of dengue concentrations, from 6.4–106 pfu/mi. However only ⅔ and ⅓ of the assays for 1.3 and 0.3 pfu/ml samples, respectively, had $C_T$ values less than background level of 40. Thus, the sensitivity of the dengue 2 fluorogenic PCR was established as approximately 6.4–10 pfu per ml. Note that the lowest virus samples are clearly distinguishable from normal sera alone, or from non-template (water) controls, indicating that background-free dengue 2 RT-PCR was achieved. FIG. 4 shows a standard curve by plotting threshold cycle ($C_T$) VS the known quantity of original virus concentrations in the reaction (pfu/ml). For practical purposes, we expressed viral concentration as pfu per ml sample rather than pfu per RT-PCR reaction. Threshold cycle decreases as the concentration of virus sample is increased to $10^6$ pfu/ml. A nearly perfect linear relationship was established between cDNA concentration and corresponding $C_T$ value over 5 logs of cDNA (r=0.973).

To demonstrate specificity of the fluorogenic PCR assay, all dengue 2 isolates from different geographic origins fisted in Table I, such as strains from Thailand, Puerto Rico, Haiti, Brazil, and Somalia were examined by the fluorogenic RT-PCR. These different dengue 2 virus genotypes were universally detected and identified by the assay. Furthermore, the assay could not detect all other flaviviruses fisted in Table I, such as dengue 1, 3 and 4 viruses, as well as other flaviviruses, including Japanese encephalitis, St. Louis encephalitis, yellow fever, and Kunjin viruses. All viruses other than dengue 2 viruses were indistinguishable from background (defined as $C_T$ of 40), indicating that the fluorogenic PCR assay is dengue 2-specific.

Detection of Immunocomplexed Dengue 2 Virus by Fluorogenic RT-PCR

It is known that dengue specific antisera can neutralize dengue virus and consequently prevent viral replication in cell lines (Johnson, 1976). Furthermore, sera specimens from Individuals with secondary dengue may contain variable amounts of non-neutralizing antibody bound to virus. Serially diluted dengue 2 virus suspensions used for previous normal sera spiking experiment (sensitivity study) were also extracted after incubating with dengue 2-specific antisera (1:500 virus reduction titer of human hyperimmune sera described in Materials and methods) at 37° C. for one hour. The resulting neutralized dengue virus was efficiently recognized and detected by fluorogenic PCR: there was no difference in $C_T$ values from assays using either native virus or immunocomplexed virus (data not shown). Thus, it was demonstrated that the fluorogenic RT-PCR could detect immunocomplexed dengue viruses that may be undetectable by conventional mosquito cell isolation.

Illustration of Dengue 2 Viremia From Natural Infection Using Fluorogenic RT-PCR.

In order to demonstrate the utility of this newly developed dengue assay, dengue 2 fluorogenic RT-PCR assay was used to quantitatively identify dengue virus from infected sera. Dengue 2 viruses were identified in clinical sera specimens collected from patients with acute febrile illness in Somalia (1993) and Haiti (1997) that yielded positive dengue 2 virus isolations. The fluorogenic assay was able to identify and confirm most of dengue 2 infections with calculated viral concentrations ranging from 10 to $6.2 \times 10^5$ pfu/ml of sera.

Figure 5:
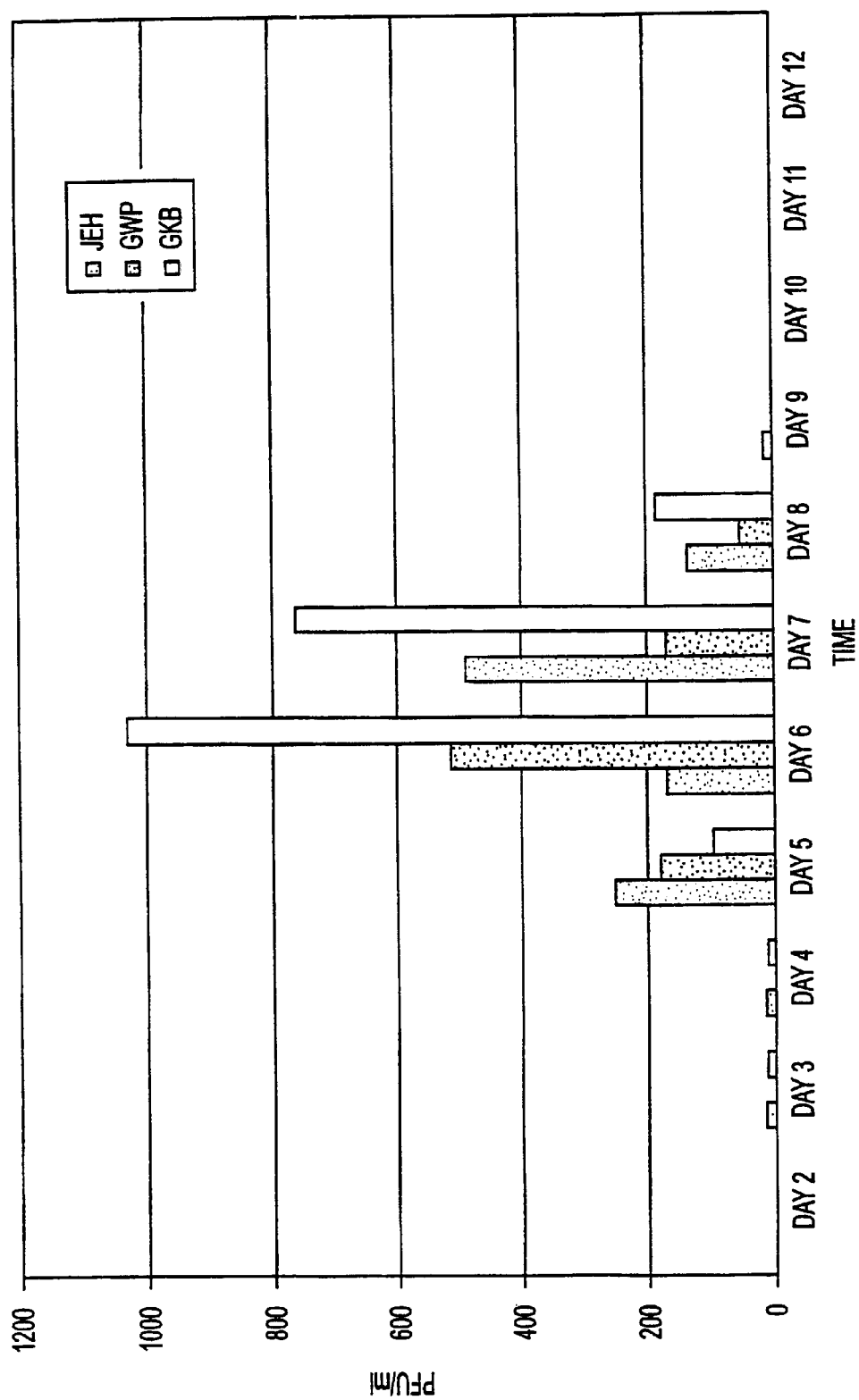
FIG. 5. Infection courses of dengue 2 S16803 in Rhesus monkey. Viral concentrations were determined from three monkeys' sera (JEH, GWP, an GKB) following subcutaneous inoculation with $10^4$ pfu dengue 2 S16803.

The fluorogenic RT-PCR assay was applied to non-human primates following experimental dengue infection with wild-type S16803 virus. Sera systematically collected daily from three rhesus monkeys from 2 through 12 days after infectious challenge (see Materials and methods) were subjected to fluorogenic RT-PCR assays. Using the dengue 2 standard curve established in this study, calculated viremia counts (expressed as pfu per ml) were determined for monkey sera as shown in FIG. 5. It was shown that two out of three monkeys had detectable low level viremia, 10 pfu/ml from day 3 after viral challenge. All three monkeys showed significant viral concentration of 40 pfu/ml or higher in sera from day 5 through day 8. Reduction of viremia to 0 pfu/ml was observed for all three monkeys after day 10.

The $C_T$ value of dengue 2 specific RT-PCR is established as reproducibly dependent on viral titer. Furthermore, zero background conditions for the assay, i.e., negative (non-template) control wells yield $C_T$ of 40 after 40 amplification cycles is systematically defined and achieved. The optimized RT-PCR protocol developed in this study allows the detection of low level viremia in infected monkey and human sera, with dengue 2 viral titers ranging from $10\mu$-$10^6$ pfu per ml. The method of the invention provides an early diagnostic capability well before infected hosts develop antibodies. In addition, virus detection can be made in hours in contrast to traditional viral isolation in mosquito cells requiring days.

Kit Packaging

As a matter of convenience, the reagents employed in the present invention can be provided in a kit packaged combination with predetermined amounts of reagents for use in determining and/or quantitating flavivirus. For example, a kit can comprise in packaged combination with other reagents any or all of primers or probes described herein. Generally, it is desirable to include the requisite number of probes and/or primers to afford identification of all of the flavivirus of interest. The oligonucleotide probes can be packaged to permit the assay to be performed in a hetero- or homogeneous format. The oligonucleotide probes can be labeled or bound to a support or can be provided with groups that permit the probe or primer to be subsequently labeled or bound to a support. The kit can further include in the packaged combination buffers, developing systems, if needed, nucleoside triphosphates and the like. Additionally, the kit may optionally contain a denaturation solution, a hybridization buffer, a wash solution and an assay device, e.g. test strip, microwell plate, etc. It is also envisioned that the kit could contain an internal calibration standard.

A standard curve of dengue 2 cDNA derived from known viral concentrations was demonstrated to have a nearly linear relationship over 5 logs, from pfu per ml, of viral concentrations. See FIG. 4. In addition to using extracted RNA from various concentrations of dengue 2, we also used serially diluted cDNA suspension to establish dengue 2 standard curve(data not shown). This standard curve would be valid only if the reverse transcription efficiency of different dengue 2 RNA concentrations is not the rate-limiting step. This assumption was preliminarily proven by examining $C_T$ values derived from viral RNA extract of spiked normal sera. However, the reverse transcription reaction does become a rate-limiting step when using RNA extracts derived from samples containing dengue virus concentrations greater than $10^7$ pfu per ml.

The following examples describe the application of the present invention for detecting and quantifying the four different dengue viruses in a sample.

EXAMPLES

Example 1

Figure 6:
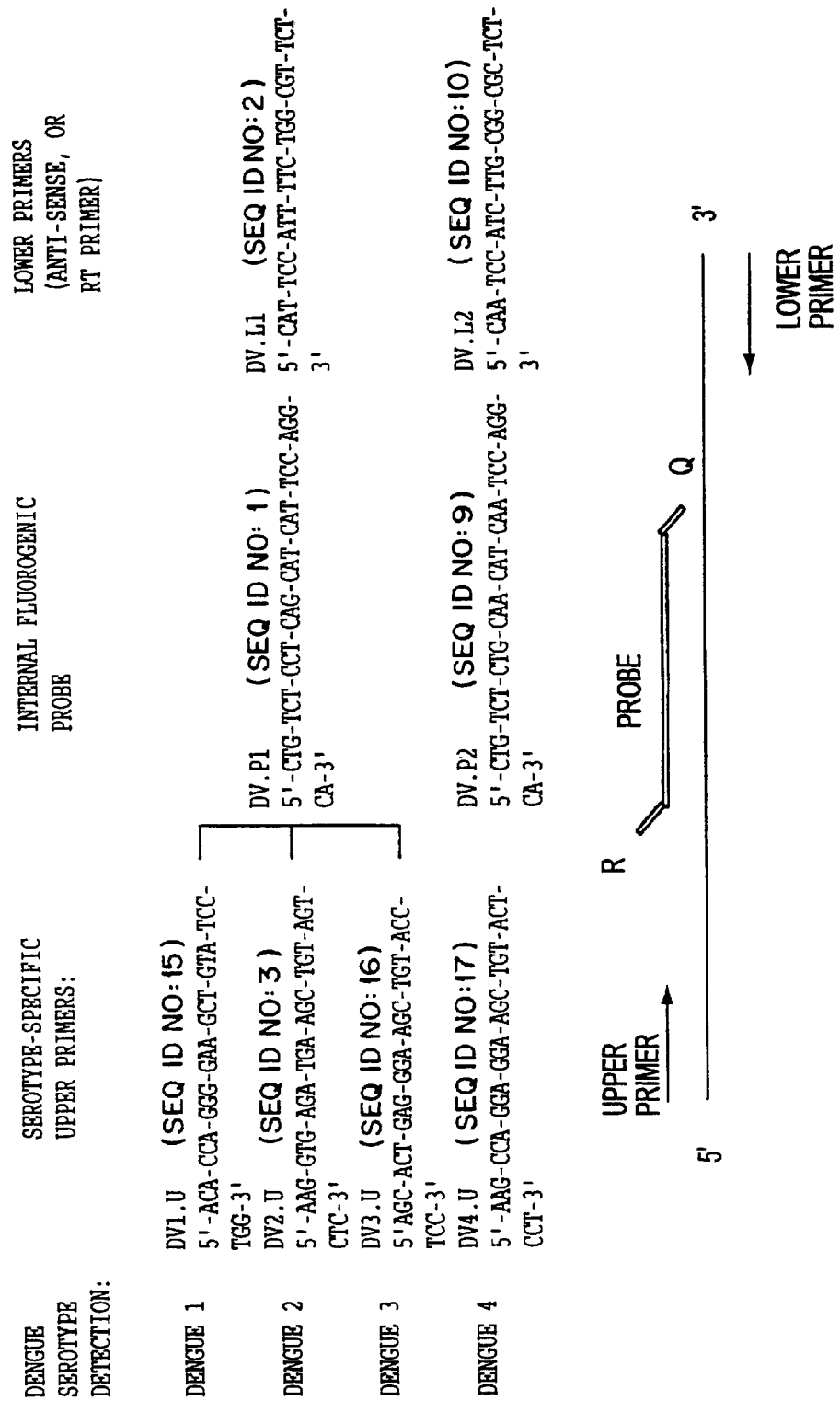
FIG. 6. The basics of the nuclease assay (SEQ ID NOS 15, 3, 1, 2, 16, 17, 9 AND 10).
Figure 7:
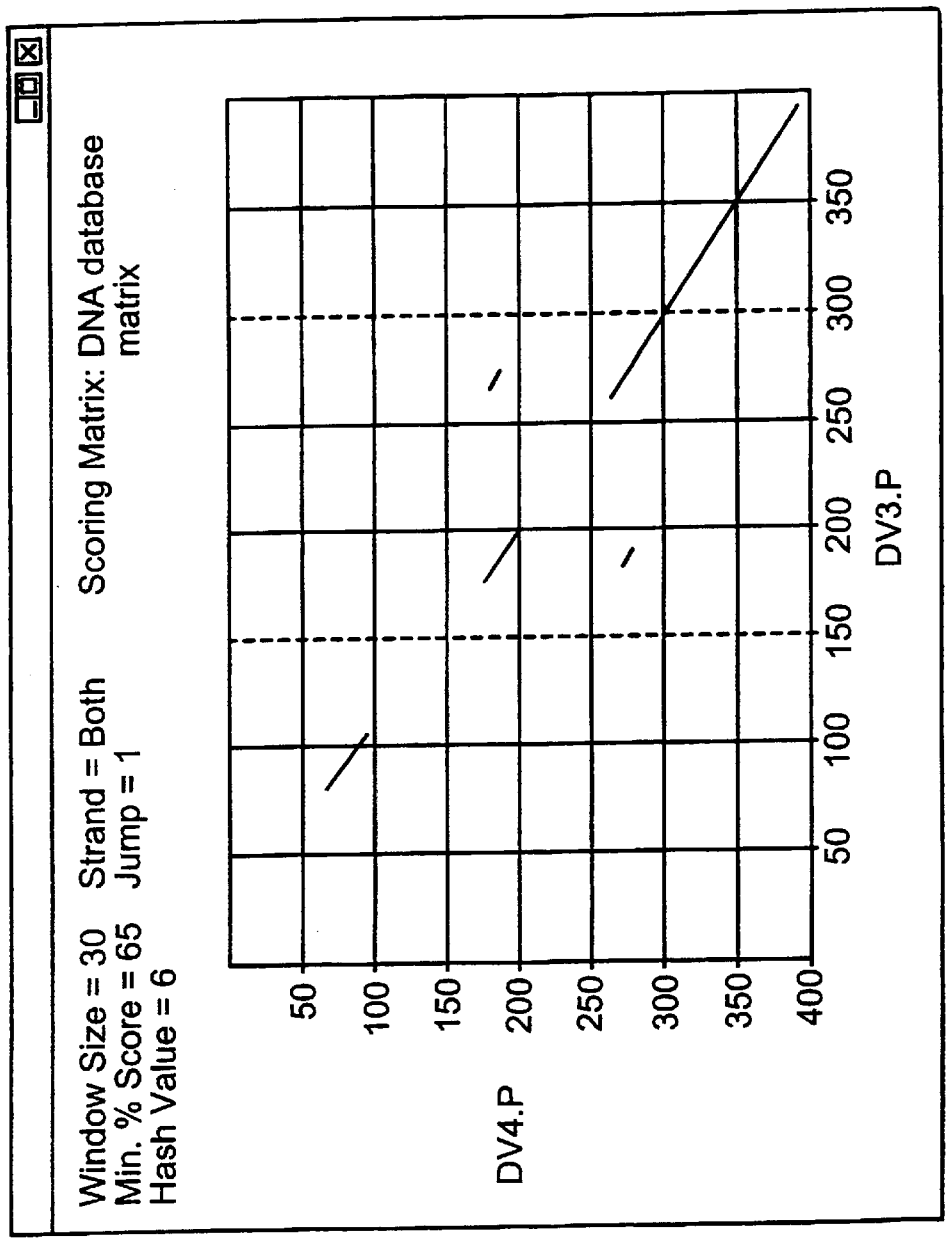
FIG. 7. Nucleic acid dot matrix analysis of the 3'-end regions for the dengue 3 and dengue 4. The last 400 bases of the 3'-end regions of these two viruses are cpared, x-axis and y-axis, dots are plotted whenever there are matches between th compared sequences. Solid lies are shown as the actual matching sequences of degue 3 and 4 for the last 160 base genomic regions. Similar extensive homologous displays are also found among all other dengue serotypes, I.e. dengue 1, 2, 3 and 4.

The Taqman assay is designed to use a specific fluorescent probe uniquely designed to bind between two primers. See FIG. 6. Both the primer set and the probe are complementary to the cDNA of interest. As the duplex strand is created, the exonuclease function of the polymerase cleaves the fluorescent analyte (R) free from its quencher (Q, resulting in a fluorescent signal upon activation. Thus, formation of a specific product can be monitored over time.

Figure 3:
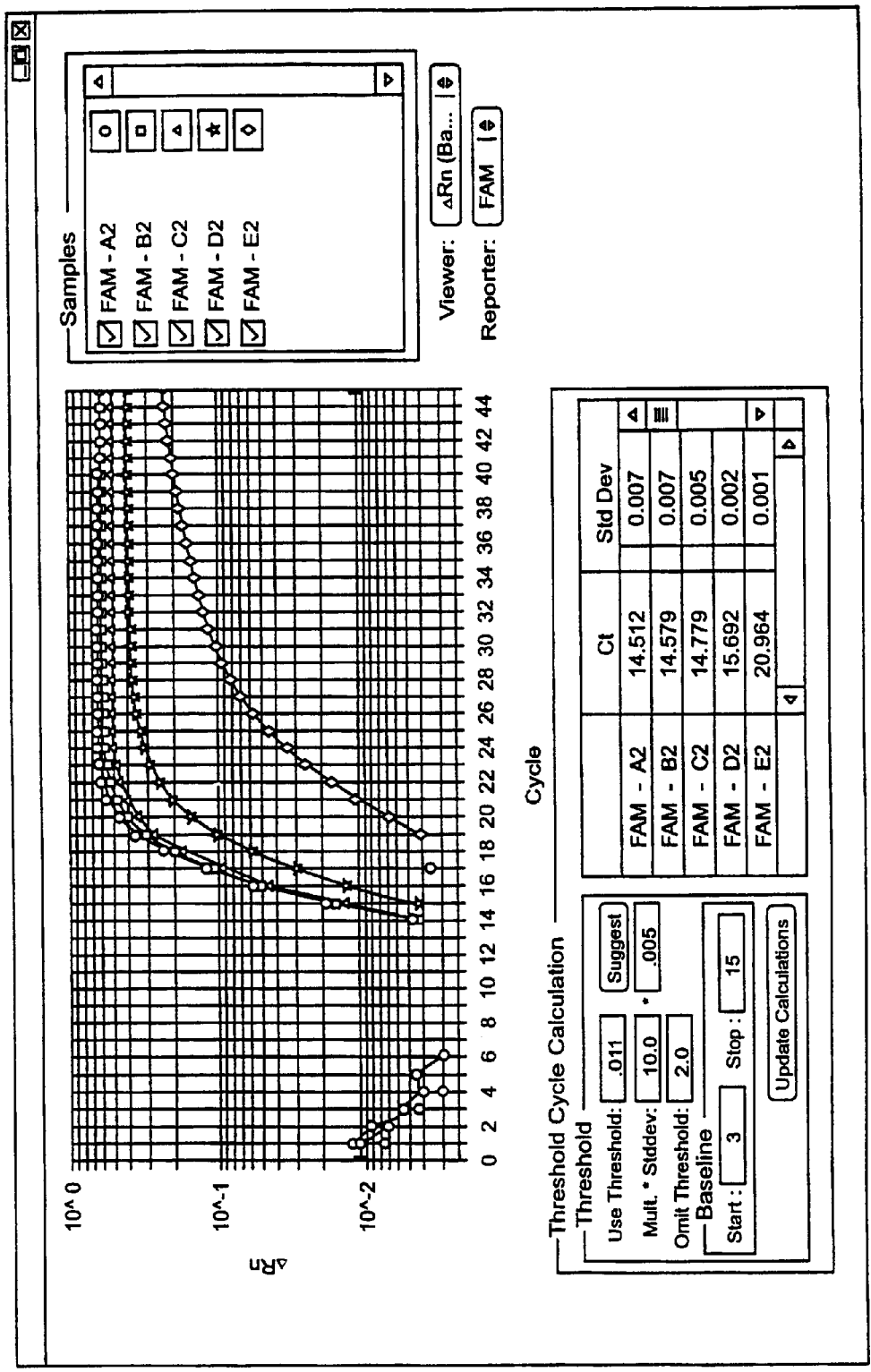
FIG. 3. Effects of $Mg^{++}$ concentrations on fluorogenic RT-PCR. Fluorescence accumulation plots derived from PCR with $MG^{++}$ concentration of 2.5, 2.0, 1.5, 1.0, and 0.5 mM are shown from left to right.

The FIGS. 1–3 show actual runs conducted using the dengue specific primers and the probes described in the application. Parallel curves demonstrate formation of the product by change in fluorescence (D R, on y- axis) with cycle number on the x-axis. As the amount of input cDNA is reduced, curves shift to the right. Product can be detected above background.

Creation of dengue cDNA is improved using dengue-specific primers in the reverse transcription (RT) step in comparison to conventional oligo-DT primers. Further, significant improvement in sensitivity (shift of detection curve to the left) when the new designed primers are used. The method results in a large cDNA product. Creation of dengue-specific product can be confirmed using a conventional dengue RT-PCR reaction using a gel.

The original development of the dengue Taqman assay utilized a single dengue-specific probe. However, the use of the single probe and primer set failed to detect other serotypes of dengue virus, notably dengue 4 viruses. The method was sensitive for dengue serotype 2 and 3 viruses, as shown in previous examples. However, dengue I virus strains were detected by modified curves in the Taqman assay. While specific for dengue serotypes 2 and 3, the original dengue-specific probe could not sensitively detect serotype 1, and not at all for serotype 4 viruses. An explanation was sought and found 'de' n the number of base mismatches in the probe(2 for serotype 1, 4 for serotype 4); this finding suggests the powerful specificity of the assay as described. Design and application of true dengue serotype-specific primers and probes.

Results of a representative Taqman assay conducted on a known dengue serotype 2 virus standard, with concentration of 8×10$^6$ plaque forming units (pfu) per milliliter. In this assay, serial 1:10 dilutions of the virus in normal human sera were extracted, reverse transcribed, and run in the Taqman polymerase chain reaction (PCR) reaction by the methods described in the application, Virus concentrations are detected by the assay as parallel curves, from most concentrated (8×10$^6$ pfu/ml) the left to a level of 80 pfu/ml at the rightmost curve. All curves are clearly distinguishable from baseline fluorescence values (bottom flat curve).

A Taqman assay conducted on a representative serum specimen collected from a patient ill with dengue in Somalia, 1993 showed a dengue serotype 2 infection. The assay was performed in blinded fashion, with no knowledge of dengue virus presence or concentration. Serial 1:10 dilutions of the test serum were extracted, reverse transcribed, and run in the Taqman polymerase chain reaction (PCR) reaction by the methods described in the application. Virus was detected by the assay as parallel curves, from most concentrated at the left to lowest concentration at the night. Again, all curves were clearly distinguishable from baseline fluorescence values (bottom flat curve). The approximate titer was estimated from standard virus titrations as about 10$^6$ pfu/ml.

An agarose gel of RT-PCR products showed the presence of sera and virus standards extracted using a conventional RNA extraction method (top gel and leftmost third of lower gel). The middle and right thirds of the lower gel show extraction of RNA from sera and virus standards using the method. The rightmost third of the lower gel shows the cDNA product obtained after titration of the virus standards, extraction of the RNA, and reverse transcription. The dengue-specific product is confirmed by the presence of bands of decreasing intensity (corresponding to dilutions of virus standard); these bands were detected using published DI and D2 dengue-specific primers.

Design of dengue serotype-specific RT-PCR assay

| Dengue serotype detected | Composition of primers and probe | | |
|---|---|---|---|
| | Upper primer | Probe | Lower primer |
| Dengue 1 | DV1-U1 | DV1-P1 | DV2-L1 |
| Dengue 2 | DV2-U2 | DV2-P1 | DV2-L1 |
| Dengue 3 | DV3-U1 | DV2-P1 | DV2-L1 |
| Dengue 4 | DV4-U1 | DV4-P1 | DV4-L1 |

This table lists the dengue-specific primers and probes. The upstream primers were designed to detect a unique region of the genome of each dengue serotype virus; details of their sequence information is present in the application.

As noted previously, detection of serotype I and 4 viruses required creation of new probes specific for each serotype (DV1-P1 and DV4-P1, respectively). The original probe and primer set is retained for detection of serotype 2 viruses; a new primer set is used along with the original probe for specific detection of serotype 3 viruses. The original downstream primers are used for the assay, except for detection of serotype 4 viruses, which require a specific downstream primer due to base mismatches in that region. Utilization of the particular primer sets and probes detailed in the slide will allow specific detection of dengue serotype viruses.

RT-PCR Plots of 10-fold serially diluted dengue 2 standard (from 8.0×1,000,000 pfu/ml) illustrated the sensitivity of the assay using the dengue-specific serotype 2 primers and probe. Titration of a virus standard (serial 10-fold dilutions) with known concentration of 8×10$^6$ pfu/ml showed detection levels as low as 0.8 pfu/ml. Resolution of positive detection from background is clearly achievable at levels of 10 pfu/ml or greater. The information shown on this plot can be used to generate a standard curve for dengue serotype 2 virus.

By plotting threshold cycle (cycle when fluorescent signal is first detected) vs. the known quantity of virus in the reaction (as expressed in pfu/ml) a standard curve for Dengue 2 RT-PCR was created. Threshold cycle drops as the quantity of input virus is increased to 10$^6$ pfu/ml, and that a straight line can be drawn between data points generated from the different dilution curves. Background fluorescence at threshold cycle 40, is off the standard curve, at the leftmost end. Test sera containing low amounts of virus (range 10–1,000 pfu/ml) could be quantitated using the standard curve.

Example 2

The Taqman assay was performed as follows:
MATERIALS
1. QiAamp viral RNA kit (Part number 29504, Qiagen Inc. 28159 Avenue Stanford, Valencia, Calif. 91355)
2. Dengue Serotype-Specific Oligonucleotide primers and Taqman probes:
Serotype-specific Upstream Primers (4):
DV1-1U (SEQ ID NO:4) 5'-GAT-CAA-GCT-TACA-CCA-GGG-GAA,GCT-GTA-TCC-TGG-3' (nucleotides 10543–10566, DV1 genome size 10718 nucleotides)
DV2-2U (SEQ ID NO:5) 5 '-GAT-CAA-GCT-TAAG-GTG-AGA-TGA-AGC-TGT-AGT-CTC-3' (nucleotides 10558–10579, DV2 genome size 10724 nucleotides)
DV3-1U (SEQ ID NO:6) 5'-GAT-CAA-GCT-TAGC-ACT-GAG-GGA-AGC-TGT-ACC-TCC-3' (nucleotides 10523–10546, DV3 genome size 10697 nucleotides)
DV4-1U SEQ ID NO:7) 5'-GAT-CAA-GCT-TAAG-CCA-GGA-GGA-AGC-TGT-ACT-CCT-3' (nucleotides 10488–10502, DV4 genome size 10645 nucleotides)
Serotype-specific Fluorescent Probes (3):
DV1-P1 (SEQ ID NO:8) 5'-CTG-TCT-CTA-CAG-CAT-CAT-TCC-AGG-CA-3' (nucleotides 10647–10672)
DV4-P1 (SEQ ID NO:9) 5'-CTG-TCT-CTG-CAA-CAT-CAA-TCC-AGG-CA-3' (nucleotides 10574–10599)

DV2-P1 (SEQ ID NO:1) 5'-CTG-TCT-CCT-CAG-CAT-CAT-TCC-AGG-CA-3' (used for both D2 and D3 viruses: nucleotides 10653–10678, DV2 genome; nucleotides 10626–1065 1, DV3 genome)

Serotype-specific Downstream Primers (2):

DV4-1L (SEQ ID NO: 10) 5'-CAA-TCC-ATC-TTG-CGG-CGC-TCT-3'+(nucleotides 10601–10621, DV4 genome size 10645 nucleotides)

DV2-1L (SEQ ID NO: 11) 5'-GAT-CGA-ATT-CCAT-TCC-ATT-TTC-TGG-CGT-TCT-3' (used for D1, D2, and D3 viruses: nucleotides 10674–10694, DV1 genome; nucleotides 10680–10700, DV2 genome; 10653–10673, DV3 genome)

3. Dengue Viruses: Dengue serotype 1, 2, 3, and 4 virus isolates and sera collected from dengue- infected humans and monkeys were Obtained from collections maintained at the Department of Virus Diseases.

4. PE Applied Biosystem 7700 Gene Detection System (Perkin Elmer, Foster City, Calif.)

5. PE Applied Biosystem 2400 cycler (Perkin Elmer, Foster City, Calif.).

Methods

A. Dengue RNA extraction (as per Qiagen kit handbook):
1. Pipette 140 ul dengue suspension (from dengue-infected Vero cell culture supemate) or serum, from dengue-infected animals into a 1.5 ml microfuge tube.
2. Add 560 ul of AVL buffer containing carrier RNA (QiAamp kit) to sample and mix well.
3. Incubate at room temperature for 10 minutes.
4. Add 560 ul of 95% ethanol to the mixture and mix thoroughly.
5. Apply 630 ul of "4" mixture to the QiAmp spin column and centrifuge at 6000×g for 1 minute.
6. Repeat step 5 by applying the rest of "4" mixture.
7. Add 500 ul AW buffer (QiAamp kit) and spin column and centrifuge at 20,000×9 for 3 minutes.
8. Repeat "step 7" and add 50 ul preheated (80° C.) molecular grade water, Centrifuge at 6004×g for 1 minute,
9. Store the obtained RNA at −20° C. fill usage for reverse transcription.

B. Reverse Transcription (RT):
1. Prepare RT master mixture as follows:

| | |
|---|---|
| 10X Taqman RT buffer | 2 ul |
| dNTPs 2.5 mM | 4 ul |
| 25 MM MgCl$_2$ | 4.4 ul |
| RNAase inhibitors 20 units/ul | 0.4 ul |
| Rtase, superscript 200 units/ul | 0.5 ul |
| RT primer (DV2.1L & DV4.11), 20 pmole/ul | 1.0 ul |

2. Mix 8 ul RNA extract with 12 ul PT master mixture.
3. Incubate at room temperature 10 minutes, followed by 30 minutes at 48° C., and inactivate the Rtase at 95° C., 5 minutes.

C. Taqman assay:
1. Prepare Dengue Taqman master mixture as follows:

| | |
|---|---|
| 10 X Taqman Buffer | 5 ul |
| dNTPs mix, 1.25 mM | 4 ul |
| MgCl$_2$, 25 mM | 4 ul |
| Dengue upper primer, 100 pmole/ul | 0.1 ul |
| Dengue lower primer, 100 pmole/ul | 0.1 ul |
| Dengue Taqman probe, 1 pmole/ul | 1.0 ul |
| Molecular grade water | 35 ul |
| AmpliTaq polymerase Gold, 5 units/ul | 0.25 ul |

The composition of primers and probe to be used for each dengue serotype-specific Taqman assay is shown in the table below.

Design of Dengue Serotype-specific RT-PCR assay

| Dengue serotype detected | Composition of primers and probe | | |
|---|---|---|---|
| | Upper primer | Probe | Lower primer |
| Dengue 1 | DV1-U1 | DV1-P1 | DV2-L1 |
| Dengue 2 | DV2-U2 | DV2-P1 | DV2-L1 |
| Dengue 3 | DV3-U1 | DV2-P1 | DV2-L1 |
| Dengue 4 | DV4-U2 | DV4-P1 | DV4-L1 |

2. Mix 2 ul of cDNA from RT reaction with 48 ul Taqman master mixture inoptical tube and capped with optical cap.
3. Place the tube into PE 7700 gene detection system, heat activate the AmpliTaq Gold 95° C. for 10 minutes followed by 40 cycles of following conditions: 95° C., 15 seconds; 60° C., minutes.

Example 3

The assay is performed according to the methodology of Example 2 using the materials below.

| | |
|---|---|
| 10X Taqman buffer | 10 µl |
| 10 mM dNTP's | 8 µl |
| 25 mM MgCl$_2$ | 8 µl |
| JE.P1 (1 pmole/ul) | 1 µl |
| JE-F214 (100 pmole/ul) | 0.2 µl |
| JE-R382 (20 pmole/ul) | 0.35 µl |
| dH$_2$O | 75 µl |
| Amplitaq-Gold | 0.25 µl |

JE.P1 (JE specific fluorescent probe(SEQ ID NO: 12)):

TCTGCTCTATCTCAACATCAGCTACTAG-GCACAGA

JE.F214 (JE RT-PCR, upstream primer(SEQ ID NO:13)): CAAGCCCCCTCGAAGCTGT

JE.R382 (JE RT-PCR, downstream primer(SEQ ID NO:14)): CACCAGCTACATACTTCGGCG

Example 4

Two panels of 4 different dengue serotypes (Dengue 1-WP74 and Den 1 Hawaii; Dengue 2-S16803 and Den 2 N6C; Dengue 3- CH53489 and Den 3 H87; Dengue 4- were used to test the specificity of fluorogenic dengue RT-PCR assays developed in this study. Viral RNA from these samples were extracted through silica dioxide method as described above. A generic dengue RT primer set comprising of two anti-sense primers (DV.L1 and DV.L2) was used to transcribe dengue viral RNA of all four possible dengue serotypes into cDNA The resultant cDNA were employed as templates for PCR amplifications using different dengue fluorogenic PCR master mixtures specially formulated for dengue serotyping.

Listing of Oligonucleotide sequences for primers and probes.

| | |
|---|---|
| DV1.P1 (SEQ ID NO: 8) | 5'-CTG-TCT-CTA-CAG-CAT-CAT-TCC-AGG-CA-3' |
| DV4.1L (SEQ ID NO: 10) | 5'-CAA-TCC-ATC-TTG-CGG-CGC-TCT-3' |
| DV2.1L (SEQ ID NO: 2) | 5'-CAT-TCC-ATT-TTC-TGG-CGT-TCT-3' |
| DV4.P1 (SEQ IID NO: 4) | 5'-CTG-TCT-CTG-CAA-CAT-CAA-TCC-AGG-CA-3' |
| DV2.P1 (SEQ ID NO: 1) | 5'-CTG-TCT-CCT-CAG-CAT-CAT-TCC-AGG-CA-3' |
| DV1.1U (SEQ ID NO: 15) | 5'-ACA-CCA-GGG-GAA-GCT-GTA-TCC-TGG-3' |
| DV2.2U (SEQ ID NO: 3) | 5'-AAG-GTG-AGA-TGA-AGC-TGT-AGT-CTC-3' |
| DV3.1U (SEQ ID NO: 16) | 5'-AGC-ACT-GAG-GGA-AGC-TGT-ACC-TCC-3' |
| DV4.1U (SEQ ID NO: 17) | 5'-AAG-CCA-GGA-GGA-AGC-TGT-ACT-CCT-3' |

The listing shows that all viral cDNA can be distinctly identified as positive by only one of the four dengue type specific master mixture, i.e., type 1, 2, 3 and 4. Only those strains yielded positive PCR product before the end of 40 cycle amplification, i.e., $C_t$ value smaller than 40, were identified as positive. This indicates that each serotype specific master can specifically detect only its own corresponding dengue serotype. There is no cross reactivity among different dengue serotypes detected by serotype-specific RT-PCR. See table below. Detection and identification of dengue strains by serotype specific 3'-based fluorogenic RT-PCR assays. Total of 40 cycles of amplification was carried out using fluorogenic PCR for dengue virus detection and identification. Positive identification was made for those samples yielded C, value of less than 40 cycles.

| Strains | Dengue 1 assay | Dengue 2 assay | Dengue 3 assay | Dengue 4 assay |
|---|---|---|---|---|
| WP74 | +++ | – | – | – |
| S16803 | – | +++ | – | – |
| CH53489 | – | – | +++ | – |
| 341750 | – | – | – | +++ |
| Den 1 Hawaii | +++ | – | – | – |
| Den 2 NGC | – | +++ | – | – |
| Den 3 H87 | – | – | +++ | – |
| Den 4 H241 | – | – | – | +++ |

| Sample ID | Den 1 Ct | Den 1 pfu/ml | Den 2 Ct | Den 2 pfu/ml | Den 3 Ct | Den 3 pfu/ml |
|---|---|---|---|---|---|---|
| 1 (D1) | 30.82 | 5559.04 | 40.00 | 0.00 | 40.00 | 0.00 |
| 1 (D1) | 31.00 | 5011.87 | 40.00 | 0.00 | 40.00 | 0.00 |
| 2 (D1) | 35.23 | 439.04 | 40.00 | 0.00 | 40.00 | 0.00 |
| 2 (D1) | 34.46 | 683.91 | 40.00 | 0.00 | 40.00 | 0.00 |
| 3 (–) | 40.00 | 0.00 | 40.00 | 0.00 | 40.00 | 0.00 |
| 3 (–) | 40.00 | 0.00 | 40.00 | 0.00 | 40.00 | 0.00 |
| 4 (D1) | 35.10 | 473.15 | 40.00 | 0.00 | 40.00 | 0.00 |
| 4 (D1) | 34.26 | 767.36 | 40.00 | 0.00 | 40.00 | 0.00 |
| 5 (–) | 40.00 | 0.00 | 40.00 | 0.00 | 40.00 | 0.00 |
| 5 (–) | 40.00 | 0.00 | 40.00 | 0.00 | 40.00 | 0.00 |
| 6 (–) | 40.00 | 0.00 | 40.00 | 0.00 | 40.00 | 0.00 |
| 6 (–) | 40.00 | 0.00 | 40.00 | 0.00 | 40.00 | 0.00 |
| 7 (D1) | 34.88 | 537.03 | 40.00 | 0.00 | 40.00 | 0.00 |
| 7 (D1) | 34.22 | 785.24 | 40.00 | 0.00 | 40.00 | 0.00 |
| 8 (D1&3) | 28.59 | 20067.81 | 40.00 | 0.00 | 33.73 | 1041.12 |
| 8 (D1&3) | 27.78 | 31988.95 | 40.00 | 0.00 | 34.06 | 860.99 |
| 9 (–) | 40.00 | 0.00 | 40.00 | 0.00 | 40.00 | 0.00 |
| 9 (–) | 40.00 | 0.00 | 40.00 | 0.00 | 40.00 | 0.00 |
| 10 (D2) | 40.00 | 0.00 | 27.23 | 43903.59 | 40.00 | 0.00 |
| 10 (D2) | 40.00 | 0.00 | 26.18 | 80352.61 | 40.00 | 0.00 |
| 11 ((D2) | 40.00 | 0.00 | 31.28 | 4265.80 | 40.00 | 0.00 |
| 11 ((D2) | 40.00 | 0.00 | 31.29 | 4241.31 | 40.00 | 0.00 |
| 12 ((D2) | 40.00 | 0.00 | 28.05 | 27384.20 | 40.00 | 0.00 |
| 12 ((D2) | 40.00 | 0.00 | 29.31 | 13258.67 | 40.00 | 0.00 |
| 15 (–) | 40.00 | 0.00 | 40.00 | 0.00 | 40.00 | 0.00 |
| 15 (–) | 40.00 | 0.00 | 40.00 | 0.00 | 40.00 | 0.00 |
| 16 (D2) | 40.00 | 0.00 | 28.14 | 26001.60 | 40.00 | 0.00 |
| 16 (D2) | 40.00 | 0.00 | 28.34 | 23173.95 | 40.00 | 0.00 |

-continued

| | | | | | | |
|---|---|---|---|---|---|---|
| 17 (D2) | 40.00 | 0.00 | 28.28 | 23988.33 | 40.00 | 0.00 |
| 17 (D2) | 40.00 | 0.00 | 28.65 | 19386.53 | 40.00 | 0.00 |
| 18 (−) | 40.00 | 0.00 | 38.40 | 70.79 | 40.00 | 0.00 |
| 18 (−) | 40.00 | 0.00 | 40.00 | 0.00 | 40.00 | 0.00 |
| 19 (D3) | 40.00 | 0.00 | 39.79 | 31.81 | 24.76 | 181970.09 |
| 19 (D3) | 40.00 | 0.00 | 40.00 | 0.00 | 24.60 | 199526.23 |
| 20 (D3) | 40.00 | 0.00 | 40.00 | 0.00 | 29.60 | 11220.18 |
| 20 (D3) | 40.00 | 0.00 | 40.00 | 0.00 | 29.87 | 9605.06 |
| 22 (D4) | 40.00 | 0.00 | 40.00 | 0.00 | 40.00 | 0.00 |
| 22 (D4) | 40.00 | 0.00 | 40.00 | 0.00 | 40.00 | 0.00 |
| 23 (D4) | 40.00 | 0.00 | 40.00 | 0.00 | 40.00 | 0.00 |
| 23 (D4) | 40.00 | 0.00 | 40.00 | 0.00 | 40.00 | 0.00 |
| 24 (−) | 40.00 | 0.00 | 40.00 | 0.00 | 40.00 | 0.00 |
| 24 (−) | 40.00 | 0.00 | 40.00 | 0.00 | 40.00 | 0.00 |
| 25 (−) | 40.00 | 0.00 | 40.00 | 0.00 | 40.00 | 0.00 |
| 25 (−) | 40.00 | 0.00 | 40.00 | 0.00 | 40.00 | 0.00 |
| 26 (D4) | 40.00 | 0.00 | 40.00 | 0.00 | 40.00 | 0.00 |
| 26 (D4) | 40.00 | 0.00 | 40.00 | 0.00 | 40.00 | 0.00 |
| 27 (−) | 40.00 | 0.00 | 40.00 | 0.00 | 40.00 | 0.00 |
| 27 (−) | 40.00 | 0.00 | 40.00 | 0.00 | 40.00 | 0.00 |
| 28 (D2&4) | 40.00 | 0.00 | 33.10 | 1496.24 | 40.00 | 0.00 |
| 28 (D2&4) | 40.00 | 0.00 | 33.03 | 1557.76 | 40.00 | 0.00 |
| 29 (D4) | 40.00 | 0.00 | 40.00 | 0.00 | 40.00 | 0.00 |
| 29 (D4) | 40.00 | 0.00 | 40.00 | 0.00 | 40.00 | 0.00 |
| 30 (D2) | 40.00 | 0.00 | 37.87 | 96.05 | 40.00 | 0.00 |
| 30 (D2) | 40.00 | 0.00 | 37.59 | 112.85 | 40.00 | 0.00 |
| 33 (D2) | 40.00 | 0.00 | 34.18 | 803.53 | 40.00 | 0.00 |
| 33 (D2) | 40.00 | 0.00 | 35.78 | 319.89 | 40.00 | 0.00 |
| 34 (D2) | 40.00 | 0.00 | 36.08 | 269.15 | 40.00 | 0.00 |
| 34 (D2) | 40.00 | 0.00 | 35.96 | 288.40 | 37.12 | 147.91 |
| 35 (D2&4) | 40.00 | 0.00 | 35.71 | 333.04 | 40.00 | 0.00 |
| 35 (D2&4) | 40.00 | 0.00 | 36.19 | 252.64 | 40.00 | 0.00 |
| 38 (−) | 40.00 | 0.00 | 39.77 | 32.17 | 40.00 | 0.00 |
| 38 (−) | 40.00 | 0.00 | 40.00 | 0.00 | 40.00 | 0.00 |
| 39 (−) | 40.00 | 0.00 | 40.00 | 0.00 | 40.00 | 0.00 |
| 39 (−) | 40.00 | 0.00 | 40.00 | 0.00 | 40.00 | 0.00 |
| 40 (−) | 40.00 | 0.00 | 40.00 | 0.00 | 40.00 | 0.00 |
| 40 (−) | 40.00 | 0.00 | 40.00 | 0.00 | 40.00 | 0.00 |
| 43 (−) | 40.00 | 0.00 | 40.00 | 0.00 | 40.00 | 0.00 |
| 43 (−) | 40.00 | 0.00 | 40.00 | 0.00 | 40.00 | 0.00 |
| 44 (D2&3) | 40.00 | 0.00 | 25.71 | 105317.37 | 38.48 | 67.61 |
| 44 (D2&3) | 40.00 | 0.00 | 25.57 | 114156.33 | 37.23 | 138.84 |
| 45 (D2) | 40.00 | 0.00 | 34.13 | 826.99 | 40.00 | 0.00 |
| 45 (D2) | 40.00 | 0.00 | 31.80 | 3162.28 | 40.00 | 0.00 |
| 46 (D4) | 40.00 | 0.00 | 40.00 | 0.00 | 40.00 | 0.00 |
| 46 (D4) | 40.00 | 0.00 | 40.00 | 0.00 | 40.00 | 0.00 |
| 47 (−) | 40.00 | 0.00 | 40.00 | 0.00 | 40.00 | 0.00 |
| 47 (−) | 40.00 | 0.00 | 40.00 | 0.00 | 40.00 | 0.00 |
| 48 (D2) | 40.00 | 0.00 | 23.15 | 459726.99 | 40.00 | 0.00 |
| 48 (D2) | 40.00 | 0.00 | 22.41 | 703882.23 | 40.00 | 0.00 |
| 49 (D2) | 40.00 | 0.00 | 35.01 | 498.31 | 40.00 | 0.00 |
| 49 (D2) | 40.00 | 0.00 | 35.27 | 429.04 | 40.00 | 0.00 |
| 50 (D2) | 40.00 | 0.00 | 35.47 | 382.38 | 40.00 | 0.00 |
| 50 (D2) | 40.00 | 0.00 | 35.72 | 331.13 | 40.00 | 0.00 |
| NTC control | 40.00 | 0.00 | 40.00 | 0.00 | 40.00 | 0.00 |
| NTC control | 40.00 | 0.00 | 40.00 | 0.00 | 39.95 | 0.00 |
| NTC control | 40.00 | 0.00 | 40.00 | 0.00 | 40.00 | 0.00 |

References

Chow, V. T. K., Seah, C. L. K. and Chan, Y. C. (1993) Use of NS-3 Consensus Primers for the Polymerase Chain Reaction Amplification and Sequencing of Dengue Viruses and Other Flaviviruses. Arch. Virol. 133, 157–170.

Eckels, K. H., Harrison, V. R., Summers, P. L. and Russell, P. K. (1980) Dengue-2 vaccine: preparation from a small-plaque virus clone. Infect. Immun. 27(1), 175–180.

Figueiredo, L. T., Batista, W. C., Kashima, S. and Nassar, E. S. (1998) Identification of Brazilian flaviviruses by a simplified reverse transcription-polymerase chain reaction method using Flavivirus universal primers. Am J Trop Med Hyg 59(3), 357–62.

Fulop, L., Barrett, A. D. T., Phillpotts, R., Martin, K., Leslie, D. and Titball, R. W. (1993) Rapid Identification of Flaviviruses Based on Conserved NS5-Gene Sequences. J. Virol. Methods 44, 79–188.

Gubler, D. J. (1989) Surveillance for dengue and dengue hemorrhagic fever. Bull. Pan. Am. Health Organ. 23, 397–404.

Harris, E., Roberts, T. G., Smith, L., Selle, J., Kramer, L. D., Valle, S., Sandoval, E. and Balmaseda, A. (1998) Typing of dengue viruses in clinical specimens and mosquitoes by single-tube multiplex reverse transcriptase PCR. J Clin Microbiol 36(9), 2634–9.

Henchal, E. A. and Putnak, J. R. (1990) The dengue viruses. Clin. Microbiol. Rev. 3(4), 376–396.

Higgins, J. A., J. Ezzell, B. J. Hinnebusch, M. Shipley, E. A. Henchal and M. S. Ibrahim. 1998.

A 5'-nuclease assay for the detection of Yersinia pestis. J. Clin. Microbiol. 36(8)-.2284–2288.

Holland P. M., R. D. Abramson, R. Watson, and D. H. Gelfand. 1991. Detection of specific polymerase chain reaction product by utilizing the 5'-3' exonuclease activity of Thermus aquaticus DNA polymerase. Proc. Natl. Acad. Sci. 88: 7276–7280.

Johnson, B. K. a. V., M. G. R. (1976) Infection of an Aedes aegypti cell fine with infectious arbovirus-antibody complexes. Trans Royal Soc Trop Med Hyg 70(3), 230–34.

Leitmeyer KC, V.D., Watts DM Salas R, Villalobos de Chacon I, Ramosa C, Rico-Hesse R. I (1999) Dengue virus structural differences that correlate with pathogenesis. J Virol 73 (6), 4738–4747.

Lewis, J.A., Chang, G.J., Lanciotti, R. S., Kinney, R. M., Mayer, L. W. and Trent, D. W. (1993) Phylogenetic Relationships of Dengue-2 Viruses. Virology 197, 216–224.

Kanesa-thasan, N., Iacono Connors, L., Magill, A., Smoak, B., Vaughn, D. W., Dubois, D., Burrous, J. and Hoke, C. H., Jr. (1994) Dengue Serotypes 2 and 3 in U.S. Forces in Somalia, Lancet 343, 678.

Monath, T. P. (1994) Dengue: The risk to developed and developing countries Proc. Natl. Acad. Sci. USA 91, 2395–2400.

Pierre, V., Drouet, M. T. and Deubel, V. (1994) Identification of Mosquito-Borne Flavivirus Sequences Using Universal Primers and Reverse Transcription Polymerase Chain Reaction. Res. Virol. 145, 93–104.

Sudiro, T. M., Ishiko, H., Green, S., Vaughn, D. W., Nisalak, A., Kalayanarooj, S., Rothman, A. L. Raengsakulrach, B., Janus, J., Kurane, I. and Ennis, F. A. (1997) Rapid diagnosis of dengue viremia by reverse transcriptase-polymerase chain reaction using 3'-noncoding region universal primers. Am. J. Trop. Med. Hyg. 56(4), 424–9.

Sudiro, T. M., Ishiko, H., Rothman, A. L., Kershaw, D. E., Green, S., Vaughn, D. W., Nisalak, A., Kalayanarooj, S. and Ennis, F. A. (1998) Microplate-reverse hybridization method to determine dengue virus serotype. J Virol Methods 73(2), 229–35.

Tanaka, M. (1993) Rapid Identification of Flavivirus Using the Polymerase Chain Reaction. Virol. Methods 41, 311–322.

Trofa, A. F., DeFraites, R. F., Smoak, B. L., Kanesa-thasan, N., King, A. D., Burrous, J. M., MacArthy, P. O., Rossi, C. and Hoke, C. H., Jr. (1997) Dengue fever in US military personnel in Haiti. Jama 277(19), 1546–8.

INCORPORATION BY REFERENCE

To the extent necessary to understand or complete the disclosure of the present invention, all publications, patents, and patent applications mentioned herein are expressly incorporated by reference therein to the same extent as though each were individually so incorporated.

What is claimed is:

1. A composition suitable for use in a process involving DNA amplification comprising DNA segments of 19–36 nucleotides in length which have sequences selected from:

Serotype-specific Upstream Primers (5)
DV1-1U 5'-GAT-CAA-GCT-TACA-CCA-GGG-GAA-GCT-GTA-TCC-TGG-3' (SEQ ID NO 4),
DV2-2U 5'-GAT-CAA-GCT-TAAG-GTC-AGA-TGA-AGC-TGT-AGT-CTC-3' (SEQ ID NO 5),
DV3-1U 5'-GAT-CAA-GCT-TAGC-ACT-GAG-GGA-AGC-TGT-ACC-TCC-3' (SEQ ID NO 6),
DV4-1U 5'-GAT-CAA-GCT-TAAG-CCA-GGA-GGA-AGC-TGT-ACT-CCT-3' (SEQ ID NO 7), and
JE.F2–5'-CAAGCCCCCTCGAAGCTGT-3' (SEQ ID NO 13);

Serotype-specific Fluorescent probes (4)
DV1-P1 5'-CTG-TCT-DTA-CAG-CAT-CAT-TCC-AGG-CA-3' (SEQ ID NO 8),
DV4-P1 5'-CTG-TCT-CTG-CAA-CAT-CAA-TCC-AGG-CA-3' (SEQ ID NO 9),
DV2-P1 5'-CTG-TCT-CCT-CAG-CAT-CAT-TCC-AGG-CA-3' (SEQ ID NO 1), and
JE.P1 5'-TCTGCTCTATCTCAACATCAGCTACTA GGCACAGA-3' (SEQ ID NO 12); and Serotype-specific Down-stream Primer (3)
DV4-1L 5'-CAA-TCC-ATC-TTG-CGG-CGC-TCT-3' (SEQ ID NO 10),
DV2-1L 5'-GAT-CGA-ATT-CCAT-TCC-ATT-TTC-TGG-CGT-TCT-3' (SEQ ID NO 11), and
JE.R382 5'-CACCAGCTACATACTTCGGCG-3' (SEQ ID NO 14); or the complement thereof, wherein the composition contains a) at least one of said serotype-specific upstream primers and one of said serotype-specific down stream primers or b) one of said serotype-specific fluorescent probes.

2. The isolated DNA segments of claim 1 wherein said segments are probes and are labeled.

3. The probe of claim 2 wherein the label is fluorescent.

4. The probe of claim 2 wherein the label is a quencher.

5. The probe of claim 2 wherein the segment is labeled at both the 3' and 5' end, respectively, where one label is a quencher and the other is a fluorescent.

6. A PCR-based diagnostic kit for detecting or quantitating a flavivirus serotype comprising: isolated DNA segments of 19–36 nucleotides which have sequences selected from:

Serotype-specific Upstream Primers (5)
DV1-1U 5'-GAT-CAA-CT-TACA-CCA-GGG-GAA-GCT-GTA-TCC-TGG-3' (SEQ ID NO 4),
DV2-2U 5'-GAT-CAA-GCT-TAAG-GTC-AGA-TGA-AGC-TGT-AGT-CTC-3' (SEQ ID NO 5),
DV3-1U 5'-GAT-CAA-GCT-TAGC-ACT-GAG-GGA-AGC-TGT-ACC-TCC-3' (SEQ ID NO 6),
DV4-1U 5'-GAT-CAA-GCT-TAAG-CCA-GGA-GGA-AGC-TGT-ACT-CCT-3' (SEQ ID NO 7), and
JE.F214 5'-CAAGCCCCCTCGAAGCTGT-3' (SEQ ID NO 13);

Serotype-specific Fluorescent probes (4)
DV1-P1 5'-CTG-TCT-DTA-CAG-CAT-CAT-TCC-AGG-CA-3' (SEQ ID NO 8),
DV4-P1 5'-CTG-TCT-CTG-CAA-CAT-CAA-TCC-AGG-CA-3' (SEQ ID NO 9),
DV2-P1 5'-CTG-TCT-CCT-CAG-CAT-CAT-TCC-AGG-CA-3' (SEQ ID NO 1), and
JE.P1 5'-TCTGCTCTATCTCAACATCAGCTACTAG GCACAGA-3' (SEQ ID NO 12); and Serotype-specific Down-stream Primer (3)
DV4-1L 5'-CAA-TCC-ATC-TTG-CGG-CGC-TCT-3' (SEQ ID NO 10),
DV2-1L 5'-GAT-CGA-ATT-CCAT-TCC-ATT-TTC-TGG-CGT-TCT-3' (SEQ ID NO 11), and
JE.R382 5'-CACCAGCTACATACTTCGGCG-3' (SEQ ID NO 14); or the complement thereof, wherein the kit contains a) at least one of said serotype-specific upstream primers and one of said serotype-specific down stream primers or b) one of said serotype-specific fluorescent probes.

7. The kit of claim 6 wherein said segments are labeled probes.

8. The kit of claim 7 wherein the label is fluorescent.

9. The kit of claim 7 wherein the label is a quencher.

10. The kit of claim 6 wherein the segment is labeled at both the 3' and 5' end, respectively, where one label is a quencher and the other is a fluorescent.

11. A method for detecting or quantifying one or more species of flavivirus contained in sample comprising the steps of:

i) collecting a sample suspected of containing a flavivirus;
ii) preparing said sample for PCR amplification;
iii) adding to said prepared sample, PCR reagents including both probes and primer pairs wherein the probes and primers in the primer pair consist of 19–36 nucleotides in lenght and contain any one of the following, Serotype-specific Upstream Primers (5)
DV1-1U 5'-GAT-CAA-GCT-TACA-CCA-GGG-GAA-GCT-GTA-TCC-TGG-3' (SEQ ID NO 4),
DV2-2U 5'-GAT-CAA-GCT-TAAG-GTC-AGA-TGA-AGC-TGT-AGT-CTC-3' (SEQ ID NO 5),
DV3-1U 5' -GAT-CAA-GCT-TAGC-ACT-GAG-GGA-AGC-TGT-ACC-TCC-3' (SEQ ID NO 6),
DV4-1U 5'-GAT-CAA-GCT-TAAG-CCA-GGA-GGA-AGC-TGT-ACT-CCT-3' (SEQ ID NO 7), and
JE.F214 5'-CAAGCCCCCTCGAAGCTGT-3' (SEQ ID NO 13);

Serotype-specific Fluorescent probes (4)
DV1-P1 5'-CTG-TCT-DTA-CAG-CAT-CAT-TCC-AGG-CA-3' (SEQ ID NO 8),
DV4-P1 5'-CTG-TCT-CTG-CAA-CAT-CAA-TCC-AGG-CA-3' (SEQ ID NO 9),
DV2-P1 5'-CTG-TCT-CCT-CAG-CAT-CAT-TCC-AGG-CA-3' (SEQ ID NO 1), and
JE.P1 5'-TCTGCTCTATCTCAACATCAGCTACT AGGCACAGA-3' (SEQ ID NO 12); and Serotype-specific Down-stream Primer (3)
DV4-1L 5'-CAA-TCC-ATC-TTG-CGG-CGC-TCT-3' (SEQ ID NO 10),
DV2-1L 5'-GAT-CGA-ATT-CCAT-TCC-ATT-TTC-TGG-CGT-TCT-3' (SEQ ID NO 11), and
JE.R382 5'-CACCAGCTACATACTTCGGCG-3' (SEQ ID NO 14); or the complement thereof,
wherein a) the primer pairs comprise at least one of said serotype-specific upstream primers and one of said serotype-specific down stream primers or b) at a least one probe is one of said serotype-specific fluorescent probes;

iv) maintaining the sample under conditions suitable for amplification;
v) detecting or quantifying one or more of the flavivirus species.

12. The method of claim 11 wherein said serotype-specific fluorescent probes of step (iii) are labeled with a fluorescent label.

13. The method of claim 11 wherein said serotype-specific fluorescent probes of step (iii) are labeled with a quencher.

14. The method of claim 11 wherein the segment is labeled at both the 3' and 5' end, respectively, where one label is a quencher and the other is a fluorescent.

15. The method of claim 11 wherein said flavivirus is Dengue.

16. The method of claim 15 wherein said Dengue virus is Dengue 1, 2, 3, or 4.

17. A method for detecting or quantifying dengue virus Serotype(s) comprising i) contacting a sample suspected of containing a flavivirus with PCR reagents, including at least two PCR primers selected from the following groups:

Serotype-specific Upstream Primers (5)
DV1-1U 5'-GAT-CAA-GCT-TACA-CCA-GGG-GAA-GCT-GTA-TCC-TGG-3' (SEQ ID NO 4),
DV2-2U 5' -GAT-CAA-GCT-TAAG-GTC-AGA-TGA-AGC-TGT-AGT-CTC-3' (SEQ ID NO 5),
DV3-1U 5' -GAT-CAA-GCT-TAGC-ACT-GAG-GGA-AGC-TGT-ACC-TCC-3' (SEQ ID NO 6),
DV4-1U 5'-GAT-CAA-GCT-TAAG-CCA-GGA-GGA-AGC-TGT-ACT-CCT-3' (SEQ ID NO 7), and
JE.F214 5'-CAAGCCCCCTCGAAGCTGT-3' (SEQ ID NO 13);

Serotype-specific Down-stream Primer (3)
DV4-1L 5'-CAA-TCC-ATC-TTG-CGG-CGC-TCT-3' (SEQ ID NO 10),
DV2-1L 5'-GAT-CGA-ATT-CCAT-TCC-ATT-TTC-TGG-CGT-TCT-3' (SEQ ID NO 11), and
JE.R382 5'-CACCAGCTACATACTTCGGCG-3' (SEQ ID NO 14), or the complement thereof, wherein the primer pairs comprise at least one of said serotype specific upstream primers and one of said serotype specific down stream primers, and a polymerase enzyme, and an oligonucleotide probe selected from the following group:

Serotype-specific fluorescent probes (4)
DV1-P1 5'-CTG-TCT-DTA-CAG-CAT-CAT-TCC-AGG-CA-3' (SEQ ID NO 8),
DV4-P1 5'-CTG-TCT-CTG-CAA-CAT-CAA-TCC-AGG-CA-3' (SEQ ID NO 9),
DV2-P1 5'-CTG-TCT-CCT-CAG-CAT-CAT-TCC-AGG-CA-3' (SEQ ID NO 1), and
JE.P1 5'-TCTGCTCTATCTCAACATCAGCTACT AGGCACAGA-3' (SEQ ID NO 12), or the complement thereof, wherein at least one of said oligonucleotide probes is a serotype specific fluorescent probe, and wherein a fluorescer molecule attached to a first end of the oligonucleotide probe and a quencher molecule attached to a second end of the oligonucleotide probe such that the quencher molecule substantially quenches the fluorescer molecule whenever the oligonucleotide probe is in the free stranded state and such that the fluorescer is substantially unquenched whenever the oligonucleotide probe is hybridized to the target nucleic acid;

a 5' end which is rendered impervious to digestion by the 5'.fwdarw.3' exonuclease activity of a polymerase; and a 3' end which is rendered impervious to the 5'.fwdarw.3' extension activity of the polymerase; and ii) subjecting the sample, oligonucleotide probe, and the PCR reagents to thermal cycling, including a polymerization step, the thermal cycling being sufficient to amplify the target nucleic acid specified by the PCR reagents.

18. The method of claim 17 further comprising the step of measuring the extent of fluorescence quenching of the oligonucleotide probe, such measurement being performed subsequent to thermocycling and at a probe hybridization temperature.

19. The method of claim 17 further comprising the step of measuring the extent of fluorescence quenching of the oligonucleotide probe at a probe hybridization temperature in a manner which locates the probe within the individual cells originally containing the target nucleic acid sequence.

20. The method of claim 17 wherein the sample, the PCR reagents, and the oligonucleotide probe are located in a containment assembly.

21. The method of claim 17 wherein the probe hybridization temperature is less than or equal to the temperature of the polymerization step of the thermocycling.

* * * * *

SEQUENCE LISTING

```
<160> NUMBER OF SEQ ID NOS:  21

<210> SEQ ID NO 1
<211> LENGTH: 26
<212> TYPE: DNA
<213> ORGANISM: Artificial Sequence
<220> FEATURE:
<223> OTHER INFORMATION: Description of Artificial Sequence: Probe

<400> SEQUENCE: 1
ctgtctcctc agcatcattc caggca                                          26

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 2
cattccattt tctggcgttc t                                               21

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 3
```
aaggtgagat gaagctgtag tctc                                      24

<210> SEQ ID NO 4
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 4
gatcaagctt acaccagggg aagctgtatc ctgg                           34

<210> SEQ ID NO 5
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 5
gatcaagctt aaggtgagat gaagctgtag tctc                           34

<210> SEQ ID NO 6
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 6
gatcaagctt agcactgagg gaagctgtac ctcc                           34

<210> SEQ ID NO 7
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 7
gatcaagctt aagccaggag gaagctgtac tcct                           34

<210> SEQ ID NO 8
<211> LENGTH: 26
<212> TYPE: DNA
<213> ORGANISM: Artificial Sequence
<220> FEATURE:
<223> OTHER INFORMATION: Description of Artificial Sequence: Probe

<400> SEQUENCE: 8
ctgtctctac agcatcattc caggca                                    26

<210> SEQ ID NO 9
<211> LENGTH: 26
<212> TYPE: DNA
<213> ORGANISM: Artificial Sequence
<220> FEATURE:
<223> OTHER INFORMATION: Description of Artificial Sequence: Probe

<400> SEQUENCE: 9
ctgtctctgc aacatcaatc caggca                                    26

<210> SEQ ID NO 10
<211> LENGTH: 21
<212> TYPE: DNA
<213> ORGANISM: Artificial Sequence

```
<220> FEATURE:
<223> OTHER INFORMATION: Description of Artificial Sequence: Primer

<400> SEQUENCE: 10
caatccatct tgcggcgctc t                                          21

<210> SEQ ID NO 11
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 11
gatcgaattc cattccattt tctggcgttc t                               31

<210> SEQ ID NO 12
<211> LENGTH: 35
<212> TYPE: DNA
<213> ORGANISM: Artificial Sequence
<220> FEATURE:
<223> OTHER INFORMATION: Description of Artificial Sequence: Probe

<400> SEQUENCE: 12
tctgctctat ctcaacatca gctactaggc acaga                           35

<210> SEQ ID NO 13
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 13 caagcccccct cgaagctgt                                            19

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 14
caccagctac atacttcggc g                                          21

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence:
    Oligonucleotide sequence used for primer or probe

<400> SEQUENCE: 15
acaccagggg aagctgtatc ctgg                                       24

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence:
    Oligonucleotide sequence used for primer or probe

<400> SEQUENCE: 16
```

```
agcactgagg gaagctgtac ctcc                                          24

<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence:
      Oligonucleotide sequence used for primer or probe

<400> SEQUENCE: 17
aagccaggag gaagctgtac tcct                                          24

<210> SEQ ID NO 18
<211> LENGTH: 390
<212> TYPE: DNA
<213> ORGANISM: Dengue virus

<400> SEQUENCE: 18
gtacggtaag agctatgctg cctgtgagcc ccgtccaagg acgtaaaatg aagtcaggcc    60
gaaagccacg gtttgagcaa accgtgctgc ctgtagcttc atcgtgggga tgtaaaaacc   120
tgggaggctg caacccatgg aagctgtacg catggggtag cagactagtg gttagaggag   180 accccctccca aaacataacg cagcagcggg gcccaacacc aggggaagct gtatcctggt   240
ggtaaggact agaggttaga ggagaccccc ggcataacaa taaacagcat attgacgctg   300
ggagagacca gagatcctgc tgtctctaca gcatcattcc aggcacagaa cgccagaaaa   360
tggaatggtg ctgttgaatc aacaggttct                                   390

<210> SEQ ID NO 19
<211> LENGTH: 399
<212> TYPE: DNA
<213> ORGANISM: Dengue virus

<400> SEQUENCE: 19
gtacggaaaa aactatgcta cctgtgagcc ccgtccaagg acgttaaaag aagtcaggcc    60
atcacaaatg ccacagcttg agtaaactgt gcagcctgta gctccacctg agaaggtgta   120
aaaaatctgg gaggccacaa accatggaag ctgtacgcat ggcgtagtgg actagcggtt   180
agaggagacc cctcccttac aaatcgcagc aacaacgggg gcccaaggtg agatgaagct   240
gtagtctcac tggaaggact agaggttaga ggagaccccc ccaaaacaaa aaacagcata   300
ttgacgctgg gaaagaccag agatcctgct gtcctctcag catcattcca ggcacagaac   360
gccagaaaat ggaatggtgc tgttgaatca acaggttct                         399

<210> SEQ ID NO 20
<211> LENGTH: 392
<212> TYPE: DNA
<213> ORGANISM: Dengue virus

<400> SEQUENCE: 20
gtacggaaga agctgtgcag cctgtgagcc ccgtccaagg acgttaaaag aagaagtcag    60
gcccaaaagc cacggtttga gcaaaccgtg ctgcctgtag ctccgtcgtg gggacgtaaa   120
gcctgggagg ctgcaaaccg tggaagctgt acgcacggtg tagcagacta gtggttagag   180
gagacccctc ccatgacaca acgcagcagc ggggcccgag cactgaggga agctgtacct   240
ccttgcaaag gactagaggt tataggagac ccccgcaaa caaaaacagc atattgacgc   300
tgggagagac cagagatcct gctgtctcct cagcatcatt ccaggcacag aacgccagaa   360
```

-continued

```
aatggaatgg tgctgttgaa tcaacaggtt ct                                     392

<210> SEQ ID NO 21
<211> LENGTH: 399
<212> TYPE: DNA
<213> ORGANISM: Dengue virus

<400> SEQUENCE: 21
gtgaaggagt tctgtaatta ccaacaacaa acaccaaagg ctattgaagt caggccactt        60
gtgccacggt ttgagcaaac cgtgctgcct gtagctccgc caataatggg aggcgtaata      120
atccccaggg aggccatgcg ccacggaagc tgtacgcgtg gcatattgga ctagcggtta      180
gaggagaccc ctcccatcac tgaaaaacgc agcaaaaggg ggcccaagcc aggaggaagc      240
tgtactcctg gtggaaggac tagaggttag aggagacccc cccaacacaa aaacagcata      300
ttgacgctgg gaaagaccag agatcctgct gtctctgcaa catcaatcca ggcacagagc      360
gccgcaagat ggattggtgt tgttgatcca acaggttct                             399
```